US006365126B1

(12) United States Patent
Zhong et al.

(10) Patent No.: US 6,365,126 B1
(45) Date of Patent: Apr. 2, 2002

(54) LEARNING AND SHORT TERM MEMORY DEFECTS WITH NEUROFIBROMATOSIS 1 (NF1) EXPRESSION

(75) Inventors: Yi Zhong; Hui-Fu Guo, both of Huntington; Jiayuan Tong, Cold Spring Harbor, all of NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/510,791

(22) Filed: Feb. 23, 2000

Related U.S. Application Data

(63) Continuation-in-part of application No. 09/046,745, filed on Mar. 24, 1998, now abandoned.
(60) Provisional application No. 60/041,469, filed on Mar. 24, 1997.

(51) Int. Cl.$^7$ ............................ A61K 49/00; C12Q 1/00
(52) U.S. Cl. ............................................. 424/9.1; 435/4
(58) Field of Search ................................ 435/4; 424/9.1

(56) References Cited

U.S. PATENT DOCUMENTS 5,859,195 A    1/1999   Collins et al. ............... 530/350

FOREIGN PATENT DOCUMENTS

WO      WO 92/00387      1/1992

OTHER PUBLICATIONS

Banfi et al. Journal of Pharmacological Methods 8:255–263 1982.*
Banfi et al. J. Pharmacological Methods 8(4):255–263 Dec. 1982; Abstract from Dialog, Medline Database.*

Silva, A.J. et al., "A Mouse Model For The Learning And Memory Deficits Associated With Neurofibromatosis Type I, " *Nature Genetics*, 15:281–284 (Mar. 15, 1997).

Silva, A.J. et al., "Un Modèle De Souris Pour Étudier Les Déficits De L'Apprentissage Et De La Mèmoire Associés Á La Neurofibromatose De Type I," *Pathologie Biologie*, 46 (9) :697–698 (Nov. 1998).

Silva, A.J., Elgersma, Y. and Costa R.M., "Molecular And Cellular Mechanisms Of Cognitive Function: Implications For Psychiatric Disorders," *Biol. Psychiatry*, 47 (3) : 200–209 (Feb. 2000).

Gutmann, D.H., "Recent Insights Into Neurofibromatosis Type I," *Arch. Neurol.*, 55:778–780 (Jun. 1998).

The, I. et al., "Rescue Of A Drosophila NF1 Mutant Phenotype By Protein Kinase A," *Science*, 276:791–794 (May 1997).

Guo, H.F. et al., "Requirement Of Drosophila NF1 For Activation Of Adenylyl Cyclase By PACAP38–Like Neuropeptides," *Science*, 276:795–798 (May 1997).

* cited by examiner

*Primary Examiner*—Robert A. Schwartzman
*Assistant Examiner*—Katharine F Davis
(74) *Attorney, Agent, or Firm*—Hamilton, Brook, Smith & Reynolds, P.C.

(57) ABSTRACT

The present invention provides methods for treating learning and short term memory defects associated with a defect in the NF1 protein. The present invention also provides methods for screening a pharmaceutical agent for its ability to treat learning and short term memory defects associated with a defect in the NF1 protein.

8 Claims, 10 Drawing Sheets

```
            1 ↓
Dm  MTQKPGEWASALLARFEDQLPNRIGAYGTQARMSQDQLVACLIHISRYRFSLVISGLTKMLQRV   64
    ||| |   ||  |||    |    |      ||| || | ||||||||| | |
Hs  MAAHRPVEWVQAVVSRFDEQLPIKTGQQNTHTKVSTEHNKECLINISKYKFSLVISGLTTILKNV   65

2 ↓
Dm  NEAALQNRHEPERCYFESLVIILTTLERCLTNQTKDTARFEEAMNVKLLLREISQFVDVQSDSNP  129
    |             | |||  ||| ||  ||||  ||| |   |||| |||| |
Hs  NNMRIFG-EAAEKNLYLSQLIILDTLEKCLAGQPKDTMRLDETMLVKQLLPEICHFLHTCREGNQ  129

Dm  NAAQLKALASKVLFALSQNHFSAVFNRISARIQELTSCSEENPDYNDIELIQHIDMDMIKLTKLL  194
    ||   || || ||| | ||||||| ||| |||||| || ||| |||  |||| |  |   || ||
Hs  HAAELRNSASGVLFSLSCNNFNAVFSRISTRLQELTVCSEDNVDVHDIELLQYINVDCAKLKRLL  194

3 ↓                                   4 ↓
Dm  QETITKFRS-KRAPPLILLYSLEKAIWNWIEYHPQEFQDLQRGTNRDISTCWEPLMDFVEYFKTE  258
    ||  || |     |||| ||| |||| |    | ||||           | |    |  |  |
Hs  KETAFKFKALKKVAQLAVINSLEKAFWNWVENYPDEFTKLYQIPQTDMAECAEKLFDLVDGF-AE  258

Dm  NKKSKTLVWPLQMLLLILNPSCLEAVVNELQQSEKEKEKDKEKVASKSAQSTSRDKDFSAKQFIE  323
    || || |||| ||||| | |                                        | |
Hs  STKRKAAVWPLQIIILLILCPEIIQDISKDVVD-------------------ENNMNKKLFLD    301

Dm  SIKRGLGQHSPSKQVTESAAIACVKLCKASTYINNTDSNNVVFKLVQFFINDLKALLFNPAKPFS  388
    |   |   | | || ||||||||||||||||||     ||| | ||| |||  ||| |||| ||
Hs  SLRKALAGHGGSRQLTESAAIACVKLCKASTYINWED-NSVIFLLVQSMVVDLKNLLFNPSKPFS  365

5 ↓
Dm  RGQGYNFADIELMIDCWVSCFRINPHNIEALKVCLNLSSPQAYHFVIVCSLLRLAHIYVDFRLQN  453
    ||    ||  || |||| |||||||||   | |   ||| ||  | | || |
Hs  RGS--QPADVDLMIDCLVSCFRISPHNNQHFKICLAQNSPSTFHYVLVNSL--------------  414

Dm  KNPFRIVNQPRLSWWPQTDVVHYRSAELRALFTDTLNKATQGYIAHTPLRYITSLTLKSKDTQ--  516
       ||   ||| | || | | |  | | || ||  ||  |  ||| |  ||| | ||||| |
Hs  ---HRIITNSALDWWPKIDAVYCHSVELRNMFGETLHKAVQGCGAHPAIRMAPSLTFKEKVTSLK  475

6 ↓
Dm  -KGLTRAEEGPAHKMLLLLLVRLIHADPTLLLNTQGKVAHEVQSSTLELINGLVSLVHQTTMPDV  580
     |  |      |||  ||   ||||||| ||| ||| |  || ||  | ||  | || |  ||
Hs  FKEKPTDLETRSYKYLLLSMVKLIHADPKLLLCNPRKQGPETQGSTAELITGLVQLVPQSHMPEI  540

Dm  AQEAMEALLALHAPEKIEVWNPEAPINTFWDVSSQVLFSISQKLIQHQIANYTDVLKWLREILIC  645
    ||||||||| ||    | ||| ||  || ||  ||  ||   || | |     | |||||||||
Hs  AQEAMEALLVLHQLDSIDLWNPDAPVETFWEISSQMLFYICKKLTSHQMLSSTEILKWLREILIC  605

Dm  RNTFLQRHKD----------YAHVGSQI------------------------------------  663
    || ||   |          || ||  |
Hs  RNKFLLKNKQADRSSCHFLLFYGVGCDIPSSGNTSQMSMDHEELLRTPGASLRKGKGNSSMDSAA  670

Dm  ------AICKQAHIKMEVVFFMYLWSVDLDAVLTSLSCFGLLCEEAEICCSSDELTVGFIMPNYH  722
          || ||   |  ||   |  |  |  | ||   |||  ||||| | |      |  |||
Hs  GCSGTPPICRQAQTKLEVALYMFLWNPDTEAVLVAMSCFRHLCEEADIRCGVDEVSVHNLLPNYN  735

7 ↓
Dm  IYQELAQLSTSATDSRICFFDNTHGNVLS--RLTLQKRIMTLLRKIEHCVHGVQPAWEETFRNWE  785
     |  |          |  |         |   |||| ||| |||||   |  ||| |  ||
Hs  TFMEFASVS---------------NMMSTGRAALQKRVMALLRRIEHPTAGNTEAWEDTHAKWE  784
```

FIG. 2A

```
Dm  VSSKVLQTYPKCKGEDGQ-AEVFHRGMGKRRASHQSSEHDLE----EQINEWANMTWFLLALGGV   845
    |||  |||| |||| ||  |    ||| |||               ||||| ||| |||||||
Hs  QATKLILNYPKAKMEDGQAAESLHKTIVKRRMSHVSGGGSIDLSDTDSLQEWINMTGFLCALGGV   849

Dm  CLHKRSSSRQMLLQQSQNNASLGSLAQNSLYSSSTSSGHGSLHPSTVSLSTLPPAPPQDVSYCPV   910
    ||  |||              ||  |     ||   |       |    |         ||
Hs  CLQQRSNS--------------GLATYSPPMGPVSERKGSM------ISVMSSEGNAD---TPV   890

8 ↓
Dm  TQFVGQLLRLLVCSNEKIGLNIQKNVKELVGEEMSTQLYPILFDQVRAIVEKFFDQQGQVNVNVT   975
    |   ||||| || ||| |||| |  ||||||   || |  |||  | ||||||||||   |||
Hs  SKFMDRLLSLMVCNHEKVGLQIRTNVKDLVGLELSPALYPMLFNKLKNTISKFFDSGQ--VLLT   953

Dm  DINTQFIEHTIYIMKSILDPKANKDPNNDQPSPSEHLGVTSIEGMMLGIVRYVRHLDMTVYAIRI   1040
    ||| || | || |||| ||                   |||| |||| ||||||| || | | |
Hs  DTNTQFVEQTIAIMKNLLD--------NHTEGSSEHLGQASIETMMLNLVRYVRVLGNMVHAIQI   1010

Dm  KTKLCQLVEVMMKRRDDLAFRQEMKFRNKLVEYLTDWVMGTSHQIAPPSSADAAILTNTSLIFRD   1105
    |||||||||||| |||||| ||||||||| ||||||||||||| ||   |||| |      ||
Hs  KTKLCQLVEVMMARRDDLSFCQEMKFRNKMVEYLTDWVMGTSNQAA---DDDVKCLT------RD   1067

Dm  LDQACMEAVAALLRGLPLQPEESDRGDLMDAKSALFLKYFTLFMNLLNDCIDSSEAEKEMNNTPL   1170
    ||||  ||| | |||||||||| | | |  || ||||||||||||||||   || | |
Hs  LDQASMEAVVSLLAGLPLQPEEGDGVELMEAKSQLFLKYFTLFMNLLNDC---SEVEDESAQT-   1127

Dm  LPPRPRMAAGKLTALRNATILAMSNLLGANIDSGLMHSIDLGYNPDLQTRAAFMEVLTQILQQGT   1235
     ||    |  |  || ||| ||||||| || |||||||| ||| | ||||| ||||| |||||
Hs  -GGRKRGMSRRLASLRHCTVLAMSNLLNANVDSGLMHSIGLGYHKDLQTRATFMEVLTKILQQGT   1191

Dm  EFDTLAETVLADRFEQLVQLVTMISDKGELPIAMALANVVTTSQMDELARVLVTLFDAKHLLSPL   1300
    ||||||||||||||| || ||||  |||||||||||||| | |  ||||||||||||  || |
Hs  EFDTLAETVLADRFERLVELVIMMGDQGELPIAMALANVVPCSQWDELARVLVTLFDSRHLLYQL   1256

Dm  LWNMFYREVEVSDCMQTLFRGNSLGSKIMAFCFKIYGASYLQMLLEPLIRPLLDEEE--ETCFEV   1363
    ||||| |  |   |||||||||| ||||| |||| ||| |||| |||| ||| |     |||
Hs  LWNMFSKEVELADSMQTLFRGNSLASKIMTFCFKVYGATYLQKLLDPLLRIVITSSDWQHVSFEV   1321

Dm  DPARLDPTEDIEQHRNNLIALTQKVFDAIINSSDRFPPQLRSMCHCLYQVLSKRFPNLLQNNIGA   1428
    ||  | || |  |  ||| | |   ||||||| | ||||||  ||||||| |||   | |||||
Hs  DPTRLEPSESLEENQRNLLQHTEKFFHAIISSSSEFPPQLRSVCHCLYQVVSQRFP---QNSIGA   1383

9 ↓
Dm  VGTVIFLRFINPAIVSPQELGIVDKQVHSSAKRGLMLMSKILQNIANHVEFSKEQHMLCFNDFLR   1493
    ||   |||||||||||| |  |||      |||||||||||| |||||| |  |||| |||| |
Hs  VGSAMFLRFINPAIVSPYEAGILDKKPPPRIERGLKLMSKILQSIANHVLFTKEEHMRPFNDFVK   1448

Dm  DHFEAGRRFFIQIASDCETVDQTSHSMSFISDANVLALHRLLWTHQEKIGDYLSSSRDHKAVGRR   1558
     |   | |||| |||||| | ||  || |||| ||||||||| |||||| ||||||||||||||
Hs  SNFDAARRFFLDIASDCPTSDAVNHSLSFISDGNVLALHRLLWNNQEKIGQYLSSNRDHKAVGRR   1513

Dm  PFDKMATLLAYLGPPEHKPVDSHMMFSSYARWSSIDMSSTNFEEIMVKHQMHEKEEFKTLKSMNI   1623
    |||||||||||||||||||| |      |||| ||| |  |||||| |||||||||| ||| |
Hs  PFDKMATLLAYLGPPEHKPVAD-------THWSSLNLTSSKFEEFMTRHQVHEKEEFKALKTLSI   1571

10 ↓
Dm  FYQAGTSKSGYPVFYYIARRYKIGETNGDLLIYHVILTLKPFCHSPFEVVIDFTHTCSDNRFRTE   1688
    ||||||||  |  ||| |||| ||| |||||||||| ||||   ||| |||| |||  |||| |
Hs  FYQAGTSKAGNPIFYYVARRFKTGQINGDLLIYHVLLTLKPYYAKPYEIVVDLTHTGPSNRFKTD   1636
```

FIG. 2B

```
Dm  FLQKWFYVLPTVAYENVHAVYIYNCNSWVREYTKFHDRILAPLKGNRKLLFLESPNKLTDFIDAE  1753
    ||  ||| |    ||  ||  ||||||||||||||||||  |   |   |  ||    |  |   |    |   |
Hs  FLSKWFVVFPGFAYDNVSAVYIYNCNSWVREYTKYHERLLTGLKGSKRLVFIDCPGKLAEHIEHE  1701

Dm  QQKLPGATLSLDEDLKVFSNALKLSHKDTKVAIKVGPTALQITSAEKTKVLAHSVLLNDVYYASE  1818
    |||||   |||  |||  ||||||| ||||| ||||| | |||||| |||  ||| ||| |||||
Hs  QQKLPAATLALEEDLKVFHNALKLAHKDTKVSIKVGSTAVQVTSAERTKVLGQSVFLNDIYYASE  1766

Dm  IEEVCLVDDNQFTLSITNESGQLSFIHNDCDNIVQAIIHIRNRWELSQPDSVTVHQKIRPKDVPG  1883
    ||| |||| |||| || | | |  |   | |||| ||||||||||||||||   || |||||||||
Hs  IEEICLVDENQFTLTIANQGTPLTFMHQECEAIVQSIIHIRTRWELSQPDSIPQHTKIRPKDVPG  1831

Dm  TLLNMALLNLGSCDPNLRTAAYNLLCALTATFDLKIEGQLLETQGLCIPSNNTIFIKSVSEKLAT  1948
    |||| |||||||| || ||||||||||| | |  ||||||||| ||||| ||| || ||     ||
Hs  TLLNIALLNLGSSDPSLRSAAYNLLCALTCTFNLKIEGQLLETSGLCIPANNTLFIVSISKTLAA  1896

Dm  NEPHLTLEFLEESIQGFQRTTIELKHLCLEYMTPWLKNLVKFCKSNDDSKKLKVSQILDKLINLT  2013
    ||||||||||||  ||  ||  |||||||||||||||  |||  ||| |||   |  ||||||   |
Hs  NEPHLTLEFLEECISGFSKSSIELKHLCLEYMTPWLSNLVRFCKHNDDAKRQRVTAILDKLITMT  1961

Dm  IDQKEMYPSVQAKIWGSIGQIPELIDMVLDNFLHKSITYGLGSPQVEIMADTAVALASANVQLVS  2078
    |    |||| |||||| |||| | |  |  |  |  | ||||  | ||||||||||| |  |||
Hs  INEKQMYPSIQAKIWGSLGQITDLLDVVLDSFIKTSATGGLGSIKAEVMADTAVALASGNVKLVS  2026

Dm  KKVITRICRVMDKSCTNPTQYLEQHMMWDDIAILGRYLLMLSFNNCLDVATSVPYLFHTITFLVC  2143
    ||| |   ||  |    ||| |||| |||||||| ||||||||| ||| ||||    |||| |||  ||||
Hs  SKVIGRMCKIIDKTCLSPTPTLEQHLMWDDIAILARYMLMLSFNNSLDVAAHLPYLFHVVTFLVA  2091

Dm  SGSLSMRASTHGLVINIIHSLCTCTNPSFSEEAQRVLRLSLDEFSLPKFYLLFGISKVKSAAVTA  2208
    | || |||||||||||||||||||  |||    ||||||||| ||||||||||||||||||||||  |
Hs  TGPLSLRASTHGLVINIIHSLCTCSQLHFSEETKQVLRLSLTEFSLPKFYLLFGISKVKSAAVIA  2156

Dm  FRSSCRHPTDKWLGNERVTQPLPADRERLSLPSLEVITDALLEIMEACMRDVPDCEWLNTWTSLA  2273
    ||||                |   |   ||  |  ||| |  | ||||||||||| |    ||  ||
Hs  FRSSYR---------DRSFSPGSYERETFALTSLETVTEALLEIMEACMRDIPTCKWLDQWTELA  2211

Dm  RSFAFCYNPALQPRALIVYGCISKSVTDHEVKQLLRILVKALES-------FNDLILIEALVMCL  2331
    | |||| || |||||| | ||||| |      ||  ||| |||||        |    ||||   |
Hs  QRFAFQYNPSLQPRALVVFGCISKRVSHGQIKQIIRILSKALESCLKGPDTYNSQVLIEATVIAL  2277

Dm  TRIQPLLRPESPIHRALFWVAISVLQLDEITLYGAGLALLEQNLHTLKSQGCFDKKETIAEVMMK  2396
    |  ||||  ||  || || ||||| ||||  || | ||||||||||  ||   |  |     |||
Hs  TKLQPLLNKDSPLHKALFWVAVAVLQLDEVNLYSAGTALLEQNLHTLDSLRIFNDKSP-EEVFMA  2341

11 ↓
Dm  TREKLEWHFKQLDHAVGLSFRSNFHFALVGHLIKGFRHPTPTTVSRTSRVLTMLLGIYAKPLHRD  2461
    |  |||| | || || ||| |||| |||||||| | |||  |  |||   |||  |   |   |
Hs  IRNPLEWHCKQMDHFVGLNFNSNFNFALVGHLLKGYRHPSPAIVARTVRILHTLLTLVNKHRNCD  2406

12 ↓
Dm  KFEVTPDSVAYLTALVAVSEEVRSRCHVKHALPRWPADLSS--------SVENGEASGGVQAIGL  2518
    ||||   ||||| || | ||||||||  ||   ||   |           |  |  |
Hs  KFEVNTQSVAYLAALLTVSEEVRSRCSLKHRKSLLLTDISMENVPMDTYPIHHGDPSYRTLKETQ  2471

13 ↓
Dm  PLSRRQKSWDILDQS----ALQFARQHKVPTLQ-------NARVLFKTQRSFS--VPTTKDPN--  2568
    || |   |   | |           | |   |        |  |  ||   ||   | |
Hs  PWSSPKGSEGYLAATYPTVGQTSPRARKSMSLDMGQPSQANTKKLLGTRKSFDHLISDTKAPKRQ  2536
```

FIG. 2C

```
              14 ↓
Dm  ---------------NATGIEERQERGSRS---------SVSNESNVLLDPEVLPDLSIQALVLT    2609
                   |  |    | | |           |||  ||||||||  ||| |  |||| ||
Hs  EMESGITTPPKMRRVAETDYEMETQRISSSQQHPHLRKVSVS-ESNVLLDEEVLTDPKIQALLLT    2600
                         15 ↓
Dm  VLATLVKYSSDEGETRVLYQYLAEGSVVFPKVFPVIHSLLDQKINNILSVSHDQVVLNSVQNIIQ    2674
    |||||||| ||    | || |||| ||||||||||| |  ||| |||  ||    ||     | |
Hs  VLATLVKYTTDEFDQRILYEYLAEASVVFPKVFPVVHNLLDSKINTLLSLCQDPNLLNPIHGIVQ    2665
                  16 ↓
Dm  NMLASED-PSQQQLHFLQSCGFGGLWRFAGPFTKYNMMGESSELFVNCLEAMVETCLPG------    2732
      |  |   |||  ||| || ||||||||||| |           ||  |  |   |  |||
Hs  SVVYHEESPPQYQTSYLQSFGFNGLWRFAGPFSKQTQIPDYAELIVKFLDALIDTYLPGIDEETS    2730
                                            17 ↓    18a
Dm  DESAPVPPSPRP------------YNLSSSLSSLTLGSPTDKAFSSESLDFYDNCPGSVSSLRRA    2785
    ||   | |||  |           ||| |  || |          |           |     |
Hs  EESLLTPTSPYPPALQSQLSITANLNLSNSMTSLA-TSQHSPGIDKENVELSPTTGHCNSGRTRH    2794
                                                  ↑
Dm  SHSKSRAKHRINDSPSH                                                   2802
      |  |   |
Hs  GSASQVQKQRSAGSFKRNSIKKIV                                           2818
```

LEARNING AND SHORT TERM MEMORY DEFECTS WITH NEUROFIBROMATOSIS 1 (NF1) EXPRESSION

RELATED APPLICATIONS

This application is a continuation-in-part application of U.S. application Ser. No. 09/046,745, filed Mar. 24, 1998, now abandoned which claims the benefit of U.S. Provisional Application No. 60/041,469, filed Mar. 24, 1997. The entire teachings of these applications are incorporated herein by reference.

GOVERNMENT SUPPORT

This invention was made with Government support, in whole or in part, under Grant Nos. NIH 5R01 NS34779-04 and NIH 5P01 HD33098-03 awarded by the National Institutes of Health. The United States government has certain rights in this invention.

BACKGROUND OF THE INVENTION

Learning, which is the modification of behavior in response to experiences, is one of the most characteristic attributes of animals, including humans. An important feature of learning is that it is adaptive. The animal, having learned, responds in ways that improve its survival and reproductive success. Different animals, even of the same species, learn things if they are exposed to different environments.

Another attribute that many animals, including humans, possess is memory of what was once experienced or learned. This attribute has been studied for many decades with much information now available that explains many of its ramifications. For example, memory can be classified as short term memory lasting seconds to minutes or as long term memory lasting days to weeks to years. Short term memory refers to the ability to recall an experience or what was learned for a short period of time. Long term memory refers to the ability to remember an experience or what was learned long after the experience has occurred or long after that which was learned.

A newly acquired experience initially is susceptible to various forms of disruption. With time, however, the new experience becomes resistant to disruption (McGaugh and Herz, *Memory Consolidation*, Albion, San Francisco, 1972; Tully, T. et al., *Cold Spring Harbor Symp. Quant. Biol.*, 55:203–211 (1990)). This observation has been interpreted to indicate that a labile, short-term memory is "consolidated" into a more stable, long-term memory.

Learning and/or memory defects impair the ability of an animal to learn and/or remember an experience, which can be detrimental to the survival and reproductive success of the animal. Accordingly, there is considerable interest in developing techniques for treating learning and/or memory defects.

SUMMARY OF THE INVENTION

The present invention relates to methods of treating a learning or short term memory defect associated with a defect in the Neurofibromatosis 1 (NF1) protein in an animal (particularly a human or other mammal or vertebrate) in need thereof. The NF1 protein defect is either a diminution in the amount of NF1 protein produced, a diminution in the activity or action of the NF1 protein produced or both a diminution in amount and activity or action of NF1 protein. In one embodiment, the method comprises administering to an animal with a learning or short term memory defect associated with a defect in the NF1 protein a NF1 compound such as exogenous NF1, NF1 analog, NF1-like moleculeogically active NF1 fragment or NF1 fusion protein. In a second embodiment, the method comprises administering to an animal with a learning or short term memory defect associated with a defect in the NF1 protein a nucleic acid sequence encoding exogenous NF1, NF1 analog, NF1-like molecule, biologically active NF1 fragment or NF1 fusion protein. In a third embodiment, the method comprises administering to an animal with a learning or short term memory defect associated with a defect in the NF1 protein an effective amount of a pharmaceutical agent that stimulates cyclic AMP formation in the same manner as NF1. In a fourth embodiment, the method comprises administering to an animal with a learning or short term memory defect associated with a defect in the NF1 protein a pharmaceutical agent that activates protein kinase A (PKA) activity in the same manner as NF1.

The present invention also relates to methods for screening a pharmaceutical agent for its ability to treat a short term memory defect associated with a defect in the NF1 protein in an animal (particularly a human or other mammal or vertebrate) in need thereof. The method comprises (a) administering a pharmaceutical agent to an animal with a short term memory defect associated with a defect in the NF1 protein; (b) training the animal under conditions appropriate to produce short term memory formation in the animal; (c) assessing short term memory formation in the animal trained in step (b); and (d) comparing short term memory formation assessed in step (c) with short term memory formation produced in the control animal to which said pharmaceutical agent has not been administered. If the short term memory formation assessed in the animal treated with the pharmaceutical agent is greater than the short term memory formation assessed in the control animal, the pharmaceutical agent is identified as one having the ability to treat a short term memory defect associated with a defect in the NF1 protein.

The invention further relates to methods for screening a pharmaceutical agent for its ability to treat a learning defect associated with a defect in the NF1 protein in an animal (particularly a human or other mammal or vertebrate) in need thereof The method comprises (a) administering a pharmaceutical agent to an animal with a learning defect associated with a defect in the NF1 protein; (b) training the animal under conditions appropriate for learning by the animal; (c) assessing learning ability in the animal trained in step (b); and (d) comparing learning ability assessed (c) with learning ability in the control animal to which said pharmaceutical agent has not been administered. If the learning ability assessed in the treated with the pharmaceutical agent is greater than the learning ability assessed in the control animal, the pharmaceutical agent is identified as one having the ability to treat a learning defect associated with a defect in the NF1 protein.

BRIEF DESCRIPTION OF THE DRAWINGS

FIGS. 2A–2D is a pictorial representation of the amino acid alignment of the Drosophila NF1 protein (SEQ ID NO:1) and human NF1 protein (SEQ ID NO:2).

DETAILED DESCRIPTION OF THE INVENTION

Figure 1A:
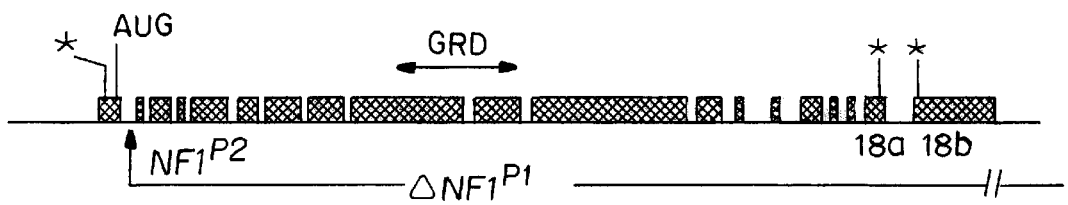
FIG. 1A is a graphical representation of the Drosophila NF1 gene.

The neurofibromatosis type 1 (NF1) tumor suppressor gene product is believed to restrict cell proliferation by functioning as a Ras-specific GTPase activating protein (Ras-GAP) (Ballester, R. et al., Cell, 63:851–859 (1990); Bernards, A., Biochim. Biophysi. Acta, 1242:43–59 (1995); Huson, S. M. et al., Brain, 111:1355–1381 (1988); McCormick, F., Curr. Opin. Genet. Dev., 5:51–55 (1995); and Xu, G. F. et al., Cell, 63:835–841 (1990)). Mutations in the NF1 gene lead to a common genetic disorder that is identified by benign tumors of the peripheral nerves, hyperpigmentation, white matter lesions in the brain, learning disabilities, and many other manifestations (Viskochil, D. et al., Annu. Rev. Neurosci., 16:183–205 (1993); McCormick, F., Curr. Opinion Genet. Dev., 5:51–55 (1995); North, K. et al., Neurology, 44:878–883 (1994)). The NF1 protein, which contains a fragment similar to the GTPase activating protein for Ras (Ras-GAP), stimulates the intrinsic activity of Ras-GTPase and therefore inhibits biological activation of Ras (Xu, G. F. et al., Cell, 62:599–608 (1990); Xu, G. F. et al., Cell, 63:835–841 (1990); Buchberg, A. M. et al., Nature, 347:291–294 (1990); Ballester, R. et al., Cell, 63.851–859 (1990); Martin, G. A. et al., Cell, 63:843–849 (1990)).

The gene responsible for human neurofibromatosis type 1 (NF1) encodes a large protein that contains a central domain related to Ras-GAPs (Huson, S. M. et al., Brain, 111:1355–1381 (1988); McCormick, F., Curr. Opin. Gen. Dev., 5:51–55 (1995); Bernards, A., Biochem. Biophys. Acta, 1242:43–60 (1995)). Loss of NF1 expression correlates with increased Ras activity in several mammalian tumor cell types (Basu, T. N. et al., Nature, 356:713–715 (1992); DeClue, J. E. et al., Cell, 69:265–273 (1992); Kim, H. A. et al., Oncogene, 11:325–35 (1995); Bollag, G., et al., Nat. Genet., 12:144–148 (1996); Largaespada, D. A. et al., Nat. Genet., 12:137–143 (1996)).

However, upon generating homozygous null mutations in a Drosophila NF1 homolog, no evidence of perturbed Ras1-mediated signaling was found, even in genetic backgrounds that reveal subtle abnormalities in Ras pathway function. Loss of NF1 causes mutants to be reduced in size and mutants also exhibit a diminished escape response. The size defect of NF1 mutants is not modified by manipulating Ras1 signaling, but is rescued by increased cyclic AMP (cAMP)-dependent protein kinase A (PKA) activity. Moreover, mutations that reduce PKA levels phenocopy NF1 mutations. These observations suggest that NF1 and PKA interact in a pathway that controls the overall growth of the organism.

The NF1 protein does not act solely to regulate Ras, but also functions as an effector mediating signaling important for differentiation. The present study of Drosophila NF1 mutants indicates that the activation of rutabaga (rut)-encoded adenylyl cyclase (Livingstone, M. S. et al., Cell, 37:205–215 (1984); Levin, L. R. et al., Cell, 68:479–489 (1992)) through heterotrimeric guanine nucleotide binding protein (G protein)-coupled receptors is regulated by the NF1 protein.

As described herein, a highly conserved Drosophila homolog of the human NF1 tumor suppressor gene has been characterized. Molecular and genetic analysis of this gene has resulted in four observations that are relevant to the study of human NF1 function. Firstly, the Drosophila NF1 protein is similar to mammalian neurofibromin over its entire length, suggesting that additional functional domains reside outside the centrally located GAP- and IRA-related segments. Secondly, the reduced size of NF1 deficient flies reflects a non-autonomous requirement for NF1, suggesting that some human NF1 symptoms may also have non-cell autonomous origins. It should be noted in this respect that a short stature is among the most common symptoms of NF1, found in approximately 30% of patients (Huson, S. M. et al.,

*Brain*, 111:1355–1381 (1988); McCormick, F., *Curr. Opin. Gen. Dev.*, 5:51–55 (1995); Bernards, A., *Biochem. Biophys. Acta*, 1242:43–60 (1995)). Thirdly, Ras1-mediated signals downstream of at least two receptor tyrosine kinases are not detectably perturbed by the complete absence of NF1. The size and behavioral phenotypes of NF1 mutants may thus reflect roles for NF1 in Ras 1-mediated pathways downstream of other receptor types, e.g., G protein-coupled receptors, or even reflect functions for NF1 unrelated to its role as a Ras regulator. Finally and most intriguingly, the size defect of NF1 mutants is not modified by manipulating Ras1 pathway components, but is mimicked by reducing PKA levels and rescued by increasing PKA activity. If NF1 and PKA do indeed function in the same pathway, one possibility is that NF1 regulates PKA activity.

Figure 1B:
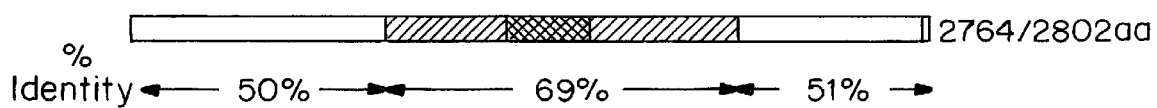
FIG. 1B is a diagram representation of the percentage amino acid identity between Drosophila and human NF1 segments.

FIGS. 1A, 1B and 2A–2D show the Drosophila NF1 gene structure and comparison of the encoded protein to human neurofibromin. FIG. 1A shows the intron-exon structure and location of translational start and stop codons. The location of a P-element in NF1$^{P2}$ and the extent of the deletion in NF1$^{P1}$ are indicated. FIG. 1B shows the percentage amino acid sequence identity between the indicated segments of Drosophila and human NF1. The GRD and IRA-related segments are drawn as black and shaded boxes, respectively. FIGS. 2A–2D shows the alignment of Drosophila (Dm) and human (Hs) NF1 proteins. Dashes were introduced to optimize the alignment. Amino acids encoded by the last complete codon in each exon are labeled with signs. The boxed segment shows the approximate extent of the GRD. Three positions where alternate splicing inserts short segments in human neurofibromin (Nishi, T. et al, *Oncogene*, 6:1555–1559 (1991); Gutmann, D. H. et al., *Hum. Mol. Genet.*, 2:989–992 (1993); Danglot, G. et al., *Hum. Mol. Gen.*, 4:915–920 (1995)) are identified by filled-in triangles. One of these locations corresponds exactly to the position where Drosophila exon 17 is joined to either exon 18a or 18b. Exon 18b includes a translational terminator after a single codon and cDNAs harboring this exon predict a protein ending in PTDKAA. Eleven (11) out of 17 Drosophila splice sites map within two codons of splice sites in the human NF1 gene (Li, Y., et al. *Genomics*, 25:9–18 (1995)).

The Drosophila homolog of NF1 is 60% identical to the human NF1 protein over its entire 2,802 anmno acid length. Although homozygous loss of NF1 is lethal in mice (Brannan, C. I. et al., *Genes & Development*, 8:1019–1029 (1994)), two viable Drosophila null mutations of NF1 have been generated. There is no NF1 protein detected by protein immunoblotting in these two mutants. NF1$^{P1}$ is a small deletion that includes the NF1 locus and at least two adjacent genes whereas NF1$^{P2}$ represents a P-element insertion. Modulation of voltage-activated K$^+$ currents (Zhong, Y. et al., *Neuron*, 14:527–536 (1995); Zhong, Y. *Nature*, 375:588–592 (1995)) induced by the neuropeptide Pituitary Adenylyl Cyclase Activating Polypeptide (PACAP38) is eliminated in these two mutant alleles.

PACAP38 (which belongs to the vasoactive intestinal polypeptide-secretin-glucagon peptide family and stimulates cAMP synthesis through G protein-coupled receptors in vertebrates (Arimura, A., *Regulatory Peptides*, 37:287–303 (1992); Spengler, D. et al., *Nature*, 365:170–175 (1993))) induces a 100-fold enhancement of K$^+$ currents by co-activating both Rut-adenylyl cyclase-cAMP and Ras-Raf kinase pathways (Zhong, Y., *Nature*, 375:588–592 (1995)). Mutations in the rut (Livingstone, M. S., et al., *Cell* 37:205–215 (1984)), Ras (Simon, M. A. et al., *Cell*, 67:701–716 (1991)), or raf (Ambrosio, L. et al., *Nature*, 342:288–291 (1989)) loci eliminate the response to PACAP38 (Zhong, Y., *Nature*, 375:588–592 (1995)). Activation of both cAMP and Ras-Raf pathways together, but not alone, mimics the PACAP38 response (Zhong, Y., *Nature*, 375:588–592 (1995)). The involvement of Ras in the PACAP38 response led to the investigation of the effect of NF1 mutations described herein.

The NF1 tumor suppressor protein partially fuinctions as a Ras-specific guanosine triphosphatase (GTPase) activating protein. Study of Drosophila NF1 mutants reveals that NF1 is essential for the cellular response to the neuropeptide PACAP38 (pituitary adenylyl cyclase-activating polypeptide) at the neuromuscular junction. The peptide induces a 100-fold enhancement of K$^+$ currents by activating the Ras-Raf and adenylyl cyclase-adenosine 3'–5' monophosphate (cAMP) pathways. This response was eliminated in NF1 mutants. NF1 appears to regulate the rutabaga-encoded adenylyl cyclase, rather than the Ras-Raf pathway. Moreover, the NF1 defect was rescued by exposure of cells to pharmacological treatment that increased concentrations of cAMP.

As described herein, a new mechanism for how G proteins activate the cAMP pathway for normal learning and memory is revealed. The G-protein activated adenylyl cyclase activity is both NF1-dependent and NF1-independent as shown in Examples 5–7. The NF1-dependent component involves the Rut-adenylyl cyclase pathway. One possibility for how NF1 regulates adenylyl cyclase activity is that NF1 acts as a GTPase activating protein (GAP) not only for the small G-protein Ras but also for heterotrirneric G-proteins. Thus, NF1 is required for a functional interaction between adenylyl cyclase and heterotrimeric G-proteins, similar to the involvement of IRA, a Ras-GAP that is distantly related to NF1, in the Ras-activated cAMP pathway in yeast (Mitts, M. R. et al., *Mol. Cell. Biol.*, 11:4591–4598 (1991)). Another possibility for how NF1 regulates adenylyl cyclase activity is that NF1 regulates adenylyl cyclase activity independently of its role as a Ras-GAP. Therefore, NF1 may be important for coordinating activities of multiple signal transduction pathways. Nevertheless, the expression of the tumour-suppressor gene NF1 and its regulation of the Rut-adenylyl cyclase signal-transduction pathway are therefore critical to the biochemical processes underlying olfactory associative, at least, learuing in Drosophila. Similar mechanisms are to be expected in vertebrates.

In summary, signaling by the PACAP38 neuropeptide is impaired in NF1 mutants and the defect is apparently caused by a blockade of PACAP38-stimulated activation of Rut-adenylyl cyclase. Thus, the NF1 protein not only acts as a negative regulator of Ras but also as a crucial component for activation of the cAMP pathway. The induced expression of a catalytic subunit of cAMP-dependent protein kinase rescues the developmental phenotype of small body size in NF1$^{P1}$ and NF1$^{P2}$ mutants, providing further support for the above conclusion.

In addition, NF1 affects learning and short-term memory independent of its developmental effects. G-protein activated adenylyl cyclase activity consists of NF1-independent and NF1-dependent components. The mechanism of the NF1-dependent activation of the Rut-adenylyl cyclase pathway is essential for mediating learning and memory.

Accordingly, the present invention encompasses methods of treating a learning defect associated with a defect in the NF1 protein or a short term memory defect associated with a defect in the NF1 protein in an animal (particularly in a human or other mammal or vertebrate) in need thereof, comprising administering to the animal an effective amount of exogenous NF1, NF1 analog, NF1-like molecule, biologically active NF1 fragment or NF1 fusion protein, or a nucleic acid sequence encoding exogenous NF1, NF1 analog, NF1-like molecule, biologically active NF1 fragment or NF1 fusion protein. In an alternative embodiment of the method of treating a learning defect associated with a defect in the NF1 protein or a short term memory defect associated with a defect in the NF1 protein in an animal in need thereof, an effective amount of a pharmaceutical agent (particularly a drug) which is capable of stimulating cyclic AMP formation in the same manner as NF1, can be administered to the animal. In another embodiment of this method, an effective amount of a pharmaceutical agent (particularly a drug) which is capable of activating protein kinase A (PKA) activity in the same manner as NF1, can be administered to the animal. As used herein, a learning or short term memory defect associated with a defect in the NF1 protein can be a recently acquired defect or a long term defect (e.g., a developmentally acquired defect). The NF1 protein defect is either a diminution in amount of NF1 protein produced, a diminution in activity or action of the NF1 protein produced or both a diminution in amount and activity or action of NF1 protein.

As used herein, the term "animal" includes mammals, as well as other animals, vertebrate and invertebrate (e.g., birds, fish, reptiles, insects (e.g., Drosophila species), Aplysia). The terms "mammal" and "mammalian", as used herein, refer to any vertebrate animal, including monotremes, marsupials and placental., that suckle their young and either give birth to living young (eutharian or placental mammals) or are egg-laying (metatharian or non-placental mammals). Examples of mammalian species include humans and other primates (e.g., monkeys, chimpanzees), rodents (e.g., rats, mice, guinea pigs) and ruminents (e.g., cows, pigs, horses).

NF1 protein can be manufactured according to methods generally known in the art. For example, NF1 can be manufactured by chemical synthesis or recombinant technology or isolated from nature (see, e.g., Sambrook et al., Eds., *Molecular Cloning: A Laboratory Manual*, 2nd edition, Cold Spring Harbor University Press, New York (1989); and Ausubel et al., Eds., *Current Protocols In Molecular Biology*, John Wiley & Sons, New York, 1997).

The exogenous NF1 can be intact protein or a functional or biologically active equivalent of NF1 protein. A functional or biologically active equivalent of NF1 protein refers to a molecule which functionally resembles (mimics) NF1. For example, a functional equivalent of NF1 can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., Eds., *Current Protocols In Molecular Biology*, John Wiley & Sons, New York, 1997).

Specifically included in the present invention are NF1 analogs, or derivatives, defmed herein as proteins having amino acid sequences analogous to endogenous NF1. Analogous amino acid sequences are defined herein to mean amino acid sequences with sufficient identity of amino acid sequence of endogenous NF1 to possess the biological activity of endogenous NF1, but with one or more "SILENT" changes in the amino acid sequence.

Also encompassed by the present invention is the administration of NF1-like molecules. NF1-like molecule, as the term is used herein, refers to a protein which functionally resembles (mimics) NF1. NF1-like molecules have the same action as NF1 and interact with the same receptor as NF1. NF1-like molecules need not have amino acid sequences analogous to endogenous NF1. NF1-like molecules can be manufactured by chemical synthesis or recombinant technology or isolated from nature as described in, for example, Ausubel et al., *Current Protocols in Molecular Biology, John Wiley & Sons, New York* (1998); and Sambrook et at, *Molecular Cloning: A Laboratory Manual*, 2nd edition, Cold Spring Harbor University Press, New York.(1989).

The present invention also encompasses the administration of biologically active polypeptide fragments of NF1. Such fragments can include only a part ofthe full-length amino-acid sequence of NF1, yet possess biological activity. Such fragments can be produced by carboxyl or amino terminal deletions, as well as internal deletions.

Also encompassed by the present invention is the administration of fusion proteins comprising NF1 proteins as described herein, referred to as a first moiety, linked to a second moiety not occurring in the NF1 protein. The second moiety can be a single amino acid, peptide or polypeptide or other organic moiety, such as a carbohydrate, a lipid or an inorganic molecule.

The present invention further encompasses biologically active derivatives or analogs of NF1 referred to herein as NF1 peptide mimetics. These mimetics can be designed and produced by techniques known to those skilled in the art. See, e.g., U.S. Pat. Nos. 5,643,873 and 5,654,276. These mimetics are based on the NF1 sequence, and peptide mimetics possess biological or functional activity similar to the biological activity or functional activity of the corresponding peptide compound, but possess a "biological advantage" over the corresponding peptide inhibitor with respect to one, or more, of the following properties: solubility, stability and susceptibility to hydrolysis and proteolysis.

Methods for preparing peptide mimetics include modifying the N-terminal amino group, the C-terminal carboxyl group and/or changing one or more of the amino linkages in the peptide to a non-amino linkage. Two or more such modifications can be coupled in one peptide mimetic inhibitor. Examples of modifications of peptides to produce peptide mimetics are described in U.S. Pat. Nos. 5,643,873 and 5,654,276.

Increased NF1 expression levels can be achieved by administration of exogenous NF1 or, alternatively, by increasing endogenous NF1 production, for example by stimulating the endogenous gene to produce increased amounts of NF1. In some animals, the amount of NF1 being produced can be of sufficient quantity, but the NF1 is abnormal in some way and, thus, cannot exert its biological effect. In this instance, providing copies of normal NF1 genes to the animal using techniques of gene transfer well known to those skilled in the art, can increase NF1 levels. Alternatively, exogenous NF1, NF1 analog, NF1-like molecule, biologically active NF1 fragment or NF1 fuision protein can be administered to increase NF1 levels.

Nucleic acid sequences are defined herein as heteropolymers of nucleic acid molecules. The nucleic acid molecules can be double stranded or single stranded and can be a deoxyribonucleotide (DNA) molecule, such as cDNA or genomic DNA, or a ribonucleotide (RNA) molecule. As such, the nucleic acid sequence can, for example, include one or more exons, with or without, as appropriate, introns, as well as one or more suitable control sequences. In one example, the nucleic acid molecule contains a single open reading frame which encodes a desired nucleic acid product. The nucleic acid sequence is operably linked to a suitable promoter.

A nucleic acid sequence encoding a desired NF1 protein, NF1 analog, NF1-like molecule, biologically active NF1 fragment or NF1 fuision protein can be isolated from nature, modified from native sequences or manufactured de novo, as described in, for example, Ausubel et al., *Current Protocols in Molecular Biology*, John Wiley & Sons, New York (1998); and Sambrook et al., *Molecular Cloning: A Laboratory Manual*, 2nd edition, Cold Spring Harbor University Press, New York. (1989). Nucleic acids can be isolated and fused together by methods known in the art, such as exploiting and manufacturing compatible cloning or restriction sites.

Typically, the nucleic acid sequence will be a gene which encodes the desired NF1 protein, NF1 analog, NF1-like molecule or NF1 fusion protein. Such a gene is typically operably linked to suitable control sequences capable of effecting the expression of the NF1 protein. The term "operably linked", as used herein, is defined to mean that the gene (or the nucleic acid sequence) is linked to control sequences in a manner which allows expression of the gene (or the nucleic acid sequence). Generally, operably linked means contiguous.

Control sequences include a transcriptional promoter, an optional operator sequence to control transcription, a sequence encoding suitable messenger RNA (mRNA) ribosomal binding sites and sequences which control termination of transcription and translation. In a particular embodiment, a recombinant gene (or a nucleic acid sequence) encoding a NF1 protein, NF1 analog, NF1-like molecule, biologically active NF1 fragment or NF1 fusion protein can be placed under the regulatory control of a promoter which can be induced or repressed, thereby offering a greater degree of control with respect to the level of the product.

As used herein, the term "promoter" refers to a sequence of DNA, usually upstream (5') of the coding region of a structural gene, which controls the expression of the coding region by providing recognition and binding sites for RNA polymerase and other factors which may be required for initiation of transcription. Suitable promoters are well known in the art. Exemplary promoters include the SV40 and human elongation factor (EFI). Other suitable promoters are readily available in the art (see, e.g., Ausubel et al., *Current Protocols in Molecular Biology*, John Wiley & Sons, Inc., New York (1998); Sambrook et al., *Molecular Cloning: A Laboratory Manual*, 2nd edition, Cold Spring Harbor University Press, New York (1989); and U.S. Pat. No. 5,681,735).

NF1 proteins, NF1 analogs, NF1-like molecules, biologically active NF1 fragments, NF1 fusion proteins and pharmaceutical agents, as well as nucleic acid sequences encoding NF1 proteins, NF1 analogs, NF1-like molecules, biologically active NF1 fragments or NF1 fusion proteins, can be administered directly to an animal in a variety of ways. The mode of administration is preferably at the location of the target cells. In a particular embodiment, administration is targeted to neurons. In a preferred embodiment, the mode of administration is intracerebroventricularly.

Administration can be directly to the central nervous system. The mode of administration can be by intrathecal injection directly into the cerebrospinal fluid by puncturing the membranes surrounding the central nervous system. Puncturing of the membranes surrounding the central nervous system is usually by lumbar puncture. Sustained dosages of NF1 proteins, NF1 analogs, NF1-like molecules, biologically active NF1 fragments, NF1 fusion proteins or pharmaceutical agents, as well as nucleic acid sequences encoding NF1 proteins, NF1 analogs, NF1-like molecules, biologically active NF1 fragments or NF1 fusion proteins, can be attained by the use of infusion pumps that are implanted surgically. Osmotic techniques can also be used.

Other routes of administration are generally known in the art and include intravenous including infusion and/or bolus injection, intrathecal, parenteral., mucosal, systemic, implant, intraperitoneal, oral, intradermal, transdermal (e.g., in slow release polymers), intramuscular, subcutaneous, topical, epidural, etc. routes. Still other routes of administration, for example, to achieve absorption through epithelial or mucocutaneous linings are known in the art. NF1 proteins, NF1 analogs, NF1-like molecules, biologically active NF1 fragments and NF1 fusion proteins can also be administered by gene therapy, wherein a DNA molecule encoding a particular therapeutic protein or peptide is administered to the animal, e.g., via a vector, which causes the particular protein or peptide to be expressed and secreted at therapeutic levels in vivo.

NF1 proteins, NF1 analogs, NF1-like molecules, biologically active NF1 fragments, NF1 fusion proteins and pharmaceutical agents, as well as nucleic acid sequences encoding NF1 proteins, NF1 analogs, NF1-like molecules, biologically active NF1 fragments or NF1 fusion proteins, can be administered together with other components of biologically active agents, such as pharmaceutically acceptable surfactants (e.g., glycerides), excipients (e.g., lactose), stabilizers, preservatives, humectants, emollients, antioxidants, carriers, diluents and vehicles. If desired, certain sweetening, flavoring and/or coloring agents can also be added.

NF1 proteins, NF1 analogs, NF1-like molecules, biologically active NF1 fragments, NF1 fusion proteins and pharmaceutical agents, as well as nucleic acid sequences encoding NF1 proteins, NF1 analogs, NF1-like molecules, biologically active NF1 fragments or NF1 fusion proteins, can be administered prophylactically or therapeutically to an animal prior to, simultaneously with or sequentially with other therapeutic regimens or agents (e.g., multiple drug regimens), including with other therapeutic regimens used for the treatment of learning or short term memory defects or for the enhancement of learning or short term memory. NF1 proteins, NF1 analogs, NF1-like molecules, biologically active NF1 fragments, NF1 fusion proteins and pharmaceutical agents, as well as nucleic acid sequences encoding NF1 proteins, NF1 analogs, NF1-like molecules, biologically active NF1 fragments or NF1 fusion proteins, that are administered simultaneously with other therapeutic agents can be administered in the same or different compositions. Two or more different NF1, NF1 analogs, NF1-like molecules, biologically active NF1 fragments, NF1 fusion proteins, nucleic acid sequences, pharmaceutical agents or combinations thereof can also be administered.

NF1 proteins, NF1 analogs, NF1-like molecules, biologically active NF1 fragments, NF1 fusion proteins and pharmaceutical agents, as well as nucleic acid sequences encoding NF1 proteins, NF1 analogs, NF1-like molecules, biologically active NF1 fragments or NF1 fusion proteins, can be formulated as a solution, suspension, emulsion or lyophilized powder in association with a pharmaceutically acceptable parenteral vehicle. Examples of such vehicles are water, saline, Ringer's solution, isotonic sodium chloride solution, dextrose solution, and 5% human serum albumin.

Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation can be sterilized by commonly used techniques. Suitable pharmaceutical carriers are described in Remington's Pharmaceutical Sciences.

An effective amount of NF1 protein, NF1 analog, NF1-like molecule, biologically active NF1 fragment or NF1 fusion protein is defined herein as that amount, or dose, of NF1, NF1 analog, NF1-like molecule, biologically active NF1 fragment or NF1 fusion protein that, when administered to an animal with a learning or short term memory defect associated with a NF1 protein defect, is sufficient for therapeutic efficacy (e.g., an amount sufficient for significantly reducing or eliminating signs or symptoms associated with a learning or short term memory defect associated with a NF1 protein defect). Similarly, an effective amount of a nucleic acid sequence encoding NF1, NF1 analog, NF1-like molecule, biologically active NF1 fragment or NF1 fusion protein is defined herein as that amount, or dose, of nucleic acid sequence encoding NF1, NF1 analog, NF1-like molecule, biologically active NF1 fragment or NF1 fusion protein that, when administered to an animal with a learning or short term memory defect associated with a NF1 protein defect, is sufficient for therapeutic efficacy (e.g., an amount sufficient for significantly reducing or eliminating signs or symptoms associated with a learning or short term memory defect associated with a NF1 protein defect).

An effective amount of a pharmaceutical agent which is capable of stimulating cyclic AMP formation in the same manner as NF1 is defined herein as that amount, or dose, of pharmaceutical agent that, when administered to an animal with a learning or short term memory defect associated with a NF1 protein defect, is sufficient for therapeutic efficacy (e.g., an amount sufficient for significantly reducing or eliminating signs or symptoms associated with a learning or short term memory defect associated with a NF1 protein defect). An effective amount of a pharmaceutical agent which is capable of stimulating cyclic AMP formation in the same manner as NF1 is also that amount, or dose, of pharmaceutical agent that, when administered to an animal, is sufficient to stimulate cyclic AMP formation in the same manner as NF1.

An effective amount of a pharmaceutical agent which is capable of activating protein kinase A in the same manner as NF1 is defined herein as that amount, or dose, of pharmaceutical agent that, when administered to an animal with a learning or short term memory defect associated with a NF1 protein defect, is sufficient for therapeutic efficacy (e.g., an amount sufficient for significantly reducing or eliminating signs or symptoms associated with a learning or short term memory defect associated with a NF1 protein defect). An effective amount of a pharmaceutical agent which is capable of activating protein kinase A in the same manner as NF1 is also that amount, or dose, of pharmaceutical agent that, when administered to an animal, is sufficient to activate protein kinase A in the same manner as NF1.

The dosage administered to an animal, including frequency of administration, will vary depending upon a variety of factors, including pharmacodynamic characteristics, mode and route of administration; size, age, sex, health, body weight and diet of the recipient; nature and extent of symptoms of the learning or short term memory defect associated with a NF1 defect being treated, kind of concurrent treatment, frequency of treatment, and the effect desired.

NF1 proteins, NF1 analogs, NF1-like molecules, biologically active NF1 fragments, NF1 fusion proteins and pharmaceutical agents, as well as nucleic acid sequences encoding NF1 proteins, NF1 analogs, NF1-like molecules, biologically active NF1 fragments or NF1 fusion proteins, can be administered in single or divided doses (e.g., a series of doses separated by intervals of days, weeks or months), or in a sustained release form, depending upon factors such as nature and extent of symptoms, kind of concurrent treatment and the effect desired. Other therapeutic regimens or agents can be used in conjunction with the present invention. Adjustment and manipulation of established dosage ranges are well within the ability of those skilled in the art.

Once an effective amount has been administered, a maintenance amount of NF1 protein, NF1 analog, NF1-like molecule, biologically active NF1 fragment, NF1 fusion protein or pharmaceutical agent, or nucleic acid sequence encoding a NF1 protein, NF1 analog, NF1-like molecule, biologically active NF1 fragment or NF1 fusion protein, can be administered to the animal. A maintenance amount is the amount of NF1 protein, NF1 analog, NF1-like molecule, biologically active NF1 fragment, NF1 fusion protein or pharmaceutical agent (or nucleic acid sequence encoding NF1 protein, NF1 analog, NF1-like molecule, biologically active NF1 fragment or NF1 fusion protein) necessary to maintain the reduction or elimination of symptoms achieved by the effective dose. The maintenance amount can be administered in the form of a single dose, or a series or doses separated by intervals of days or weeks (divided doses). Second or subsequent administrations can be administered at a dosage which is the same, less than or greater than the initial or previous dose administered to the animal. Determination of such amounts are well within the ability of those skilled in the art.

The present invention also relates to methods for screening a pharmaceutical agent for its ability to treat a short term memory defect associated with a defect in the NF1 protein in an animal (particularly a human or other mammal or vertebrate) in need thereof. The method comprises (a) administering a pharmaceutical agent to an animal with a short term memory defect associated with a defect in the NF1 protein; (b) training the animal under conditions appropriate to produce short term memory formation in the animal; (c) assessing short term memory formation in the animal trained in step (b); and (d) comparing short term memory formation assessed in step (c) with short term memory formation produced in the control animal to which said pharmaceutical agent has not been administered. If the short term memory formation assessed in the animal treated with the pharmaceutical agent is greater than the short term memory formation assessed in the control animal, the pharmaceutical agent can be categorized as having the ability to treat a short term memory defect associated with a defect in the NF1 protein.

The invention furter relates to methods for screening a pharmaceutical agent for its ability to treat a learning defect associated with a defect in the NF1 protein in an animal (particularly a human or other mammal or vertebrate) in need thereof. The method comprises (a) administering a pharmaceutical agent to an animal with a learning defect associated with a defect in the NF1 protein; (b) training the animal under conditions appropriate for learning by the animal; (c) assessing learning ability in the animal trained in step (b); and (d) comparing learning ability assessed in step (c) with learning ability in the control animal to which said pharmaceutical agent has not been administered. If the learning ability assessed in the animal treated with the pharmaceutical agent is greater than the learning ability assessed in the control animal, the pharmaceutical agent can be categorized as having the ability to treat a learning. defect associated with a defect in the NF1 protein.

Pharmaceutical agents, as the term is used herein, encompasses drugs, chemical compounds, ionic compounds, organic compounds, organic ligands, including cofactors, saccharides, recombinant and synthetic peptides, proteins, peptoids, and other molecules and compositions Training of animals for short term memory formation and learning are conducted using methods generally known in the art (see, e.g., Josselyn et al., *Society for Neurosci.*, 24:926, Abstract 365.10 (1998); Casella and Davis, *Physiol. Behav.*, 36:377–25 383 (1986); Guzowski et al., *Proc. Natl. Acad. Sci. USA*, 94:2693–2698 (1997); Lamprecht et al., *J. Neuroscience*, 17(21):6443–6450 (1997): Bourtchuladze et al., *Cell*, 79:59–68 (1994); Kogan et al., *Curr. Biol.*, 7:1–11 (1996); Tully and Quinn, *J. Comp. Physiol. A Sens. Neural. Behav. Physiol.*, 157:263–277 (1985); Tully et al., *Cell*, 79:35–47 (1994)).

Pharmaceutical agents, such as drugs, chemical compounds, ionic compounds, organic compounds, organic ligands, including cofactors, saccharides, recombinant and synthetic peptides, proteins, peptoids, and other molecules and compositions, can be individually screened or one or more pharmaceutical agent(s) can be tested simultaneously for the ability to treat a learning or short term memory defect associated with a defect in the NF1 protein in accordance with the methods herein. Where a mixture of pharmaceutical agents is tested, the pharmaceutical agents selected by the methods described can be separated (as appropriate) and identified by suitable methods (e.g., PCR, sequencing, chromatography). The presence of one or more pharmaceutical agents in a test sample having the ability to treat a learning or short term memory defect associated with a defect in the NF1 protein can also be determined according to these methods.

Large combinatorial libraries of pharmaceutical agents (e.g., organic compounds, recombinant or synthetic peptides, peptoids, nucleic acids) produced by combinatorial chemical synthesis or other methods can be tested (see e.g., Zuckerman, R. N. et al., *J. Med. Chem.*, 37:2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). The teachings of these references are incorporated herein by reference. Where pharmaceutical agents selected from a combinatorial library carry unique tags, identification of individual pharmaceutical agents by chromatographic methods is possible.

Chemical libraries, microbial broths and phage display libraries can also be tested (screened) for the presence of one or more pharmaceutical agent(s) which is capable of treating a learning or short term memory defect associated with a defect in the NF1 protein in accordance with the methods herein.

Pharmaceutical agents identified in accordance with the screening methods herein can be administered to an animal with a learning or short term memory defect associated with a NF1 protein defect in the treatment of the learning or short term memory defect associated with a NF1 protein defect in accordance with the methods herein.

The invention also provides a method for assessing whether a learning or short term memory defect is associated with a defect in the NF1 protein comprising measuring the production of cAMP in tissue (particularly brain tissue) from an animal that exhibits a learning or short term memory defect. An NF1 protein defect is manifested by a loss of cAMP formation. This loss can be measured directly or, alternatively, by determining the lack of activity of protein kinase A which is activated by cAMP. Methods for measuring cAMP and protein kinase A activity are generally known in the art. In a particular embodiment, the NF1 level can subsequently be assessed and compared to the NF1 level present in a control animal.

The invention firther provides a method for assessing whether a learning or short term memory is associated with a defect in the NF1 protein comprising measuring protein kinase A activity in tissue (particularly brain tissue) from an animal that exhibits a learning or short term memory defect. An NF1 protein defect is manifested by a loss of protein kinase A activity. In a particular embodiment, the NF1 level can subsequently be assessed and compared to the NF1 level present in a control animal.

The present invention provides methods for preventing diseases associated with a defect in the NF1 protein. These diseases include neurofibromatosis type 1, benign tumors, malignant tumors, short stature, hyperpigmentation, white matter lesions in the brain and learning disabilities. In one embodiment, the diseases can be prevented by the administration of the NF1 protein, or biologically active homolog, itself or an inducible gene which codes for either the NF1 protein or a biologically active homolog of the NF1 protein. In a second embodiment, the diseases are also prevented by the administration of a NF1 analog, NF1-like molecule, biologically active NF1 fragment or NF1 fusion protein or a nucleic acid encoding a NF1 analog, NF1-like molecule, biologically active NF1 fragment or NF1 fusion protein.

In another aspect of the present invention, an assessment can be made of whether diseases are associated with a defect in the NF1 protein by measuring the production of cAMP in tissue from an animal that exhibits one or more of the diseases. An NF1 protein defect is manifested by a loss of cAMP formation. This loss can be measured directly or, alternatively, by determining the lack of activity of protein kinase A which is activated by cAMP. Methods for measuring cAMP and protein kinase A activity are generally known in the art. In a particular embodiment, the NF1 level can subsequently be assessed and compared to the NF1 level present in a control animal.

In still another aspect of the present invention, the ability of a given compound to induce or stimulate the production of cAMP can be determined by incubating the compound with two separate cellular preparations that differ from each other by the NF1 protein content. In one cellular preparation, NF1 protein is present; in the second preparation, NF1 protein is either absent or it is inactive. If a difference is noted in the amount of cAMP produced by the two preparations, with the preparation containing NF1 protein producing more cAMP than the preparation lacking NF1 protein, the compound can be categorized as having the property of inducing or stimulating the production of cAMP.

In another aspect of the present invention, an assessment can be made of whether diseases are associated with a defect in the NF1 protein by measuring protein kinase A activity in tissue from an animal that exhibits one or more of the diseases. An NF1 protein defect is manifested by a loss of protein kinase A activity. In a particular embodiment, the NF1 level can subsequently be assessed and compared to the NF1 level present in a control animal.

In yet another aspect of the present invention, the ability of a given compound to activate protein kinase A activity can be determined by incubating the compound with two separate cellular preparations that differ from each other by the NF1 protein content. In one cellular preparation, NF1 protein is present; in the second preparation, NF1 protein is either absent or it is inactive. If a difference is noted in the activity of protein kinase A by the two preparations, with the preparation containing NF1 protein having more protein kinase A activity than the preparation lacking NF1 protein, the compound can be categorized as having the property of activating protein kinase A activity.

The present invention will now be illustrated by the following examples, which are not to be considered limiting in any way.

EXAMPLES

Example 1

Characterization of the Drosophila NF1 Gene

To analyze NF1 function in an organism amenable to genetic analysis, a conserved Drosophila NF1 homolog was identified. Drosophila NF1 clones were isolated by screening a Canton-S λ, Fix II genomic phage library (Stratagene) in 25'7/0 formamide at 37° C. with a probe representing the C-terminal 1598 amino acids of human NF1. All clones identified represented the same locus. A 13,295 bp segment representing the entire gene was sequenced. A set of 32 overlapping cDNAs was isolated from eye disc, total disc and mixed stage embryo libraries and used to determine 9,750 bp of overlapping cDNA sequence. The genomic and cDNA sequences differ in multiple locations, but none of these polymorphisms affect the equence of the encoded protein. The GenBank accession numbers for the genomic and alternatively spliced cDNA sequences are L26500, L26501 and L26502.

Comparing 13,295 bp of genomic and 9,750 bp of cDNA sequence shows that Drosophila NF1 consists of 17 constitutive and 2 alternatively spliced exons 18a and 18b. The alternatively spliced cDNAs predict proteins of 2,764 and 2,802 amino acids that are 60% identical to the human NF1 protein, neurofibromin (FIGS. 1A, 1B and 2A–2D). Sequence similarity is observed over the entire length of the proteins, including regions outside of the catalytic GAP-related domain (GRD) or the more extensive segment related to yeast IRA proteins (Xu, G. et al., *Cell*, 62:599–608 (1990)). No related sequences were identified during low stringency screens of several cDNA and genomic libraries, indicating that the identified gene is the only Drosophila NF1 homolog. RNA in situ hybridization and staining of embryos and imaginal discs with monoclonal antibodies against the Drosophila protein indicate that NF1 is widely expressed at low levels during all developmental stages. In situ hybridization with single-stranded digoxygenin labeled probes and antibody staining of whole-mount preparations was performed as described (Patei, N. H., in Drosophila melanogaster: *Practical Uses in Cell and Molecular Biology*, Goldstein, L. S. B. and Fyrberg, E. A., Eds., Academic Press, San Diego, 1994). Monoclonal antibodies against Drosophila NF1 were generated, after immunizing mice with an affinity purified His-tagged fusion protein representing the C-terminal 450 residues of the longer isoform. The Drosophila NF1 gene was mapped to cytogenetic interval 96F and subsequently localized to a 30 kb DNA segment between the bride of sevenless gene and the Enhancer of split [E(spl)] complex. The NF1 homolog was mapped to cytogenetic interval 96F by in situ hybridization of biotinylated probes to salivary gland chromosomes (Engels, W. R. et al., *Focus*, 8:6–8; (1996). Using available genomic clones from this region, the gene was subsequently sublocalized to the 30 kb interval between the bride of sevenless and E(spl) loci. This deficiency uncovers the NF1 locus (Hart, A. C. et al., *Genes and Devel.*, 4:1835–1847 (1990)).

To isolate mutant alleles at the NF1 locus, 'local hops' from a strain (K33), which harbors a P-element transposon within the E(spl) complex, approximately 15 kb downstream of NF1, were generated. Inverse PCR was used to screen. Flies were raised on standard medium and crosses carried out at 25° C. To generate NF1 mutants, w;P[w] males homozygous for a P[w] transposon in 96F were crossed to virgin Ki pP Δ2–3 transposase bearing females. Single $F_t$ dysgenic males of genotype w;P[lacZw]/Kip$^P$Δ2–3 were crossed to w; TM3/TM6B virgin females. Single $F_2$ males of genotype w; P[IacZw]/TM3 or w; P[IacZw]/TM6B were crossed to w;TM3/TM6B virgin females to establish lines with stable novel P-element integrations. The red eyed progeny of this cross was analyzed in pools by inverse PCR (Dalby, B. et al., *Genetics*, 139:757–766 (1995). Among 1,600 lines screened, two showed evidence of de novo transposon insertions within the NF1 gene. Sequence analysis of cloned insertion sites and detailed mapping showed that in one mutant allele, NF1$^{P1}$, a deletion has removed all of the NF1 gene except for the first exon (FIG. 1A). The deletion extends from the first NF1 intron to the site of the original P-element insertion and as a consequence also removes at least two E(spl) transcripts. The other allele, NF1$^{P2}$, contains a P-element in the first NF1 intron (FIG. 1A). Both alleles fail to express any detectable NF1 protein and hence represent null mutations at this locus.

Unlike NF1-deficient mice (Brannan, C. I. et al., *Genes Dev.*, 8:1019–1029 (1994); Jacks, T. et al., *Nature Genetics*, 7;353–361 (1994)), Drosophila NF1 mutants are viable and can be maintained as robust homozygous stocks. However, while heterozygotes (NF1/+) show no obvious defects, homozygotes (NF1/NF1) of either allele are 25–30% smaller than the parental K33 strain during all post-embryonic stages. This growth defect is apparent under a variety of culture conditions and mutant anirnals do not display delayed eclosion or bristle phenotypes that are observed with several Minute mutations (Kongsuwan, K. et al., *Nature*, 317:555–558 (1985)). The growth defect is fully rescued by expression of an inducible hsNF1 transgene. A hsp70-NF1 mini gene was generated by cloning a hybrid cDNA/genomic NF1 insert into the Sacil and Kpn1 sites of the pKB176PL P-element vector (Basler, K. et al., *Science*, 243:931–934 (1989)). The genomic segment of the insert harbors three introns and is flanked by MluI and Esp3I sites. This vector was introduced into the germline of w$^{1118}$ flies. Rescue was obtained with daily, 30 minute 37° C. heat shocks.

To determine whether reduced cell proliferation or impaired cell growth underlies the smaller size of NF1 mutants, the wings of wild-type and mutant animals were compared. The linear dimensions of NF1 mutant wings are 25–30% smaller than those of wild-type flies. Since each wing epidermal cell secretes a single hair, cell densities can be determined by counting the number of hairs in a defined region (Dobzhansky, T., *Wilhelm Roux' Archiv fuer Entwicklungsmechanik der Organismen*, 115:363–379 (1929)). Using this approach, both homozygous NF1 mutants were found to have a 30–40% higher cell density compared to the parental line. Thus, at least in the wings, reduced cell size contributes significantly to the reduction in overall dimensions, implicating NF1 in a process which regulates cell growth. To determine whether the reduced size of wing epidermal cells reflects a cell autonomous defect, X-irradiation was used to induce mitotic recombination in the wings of heterozygous NF1 mutants, using bald and forked bristle markers to distinguish homozygous mutant clones from surrounding tissue. Clonal analysis was performed in aforked OQ background. Females of genotype f:bld P[f+]TM3 Ser were crossed to either NF1$^{P1}$, NF1$^{P2}$ or K33 males. Parents were removed after 24 hrs and the larval progeny x-irradiated (1000 Rads) after 48–72 hrs. Adult F$_1$ males of genotype f:bld P[f+]/NF1$^{P1}$ or f;bld P[f+]/+ were analyzed. No difference in the distance between wing hairs was observed between multiple NF1$^-$/clones and surrounding tissue. The reduced size of wing cells therefore reflects a non-autonomous requirement for NF1, perhaps reflecting a hormonal deficiency or impaired nutrition or metabolism. However, while smaller cells contribute to the reduced size of wings, the eyes of NF1 mutants show a reduced number of ommatidia of normal size and structure. Furthermore, NF1 deficient embryos are of normal size. Thus, loss of NF1 affects the growth of different tissues in different ways.

Example 2

Investigation of the Role of the NF1 Gene Product on Ras Function

Since the only known biochemical property of the NF1 protein is its ability to negatively regulate Ras (Basu, T. N. et al., *Nature*, 356:713–715 (1992); DeClue, J. E. et al., *Cell*, 69:265–273 (1992); Kim, H. A. et al., *Oncogene*, 11:325–335 (1995); Bollag, G. et al., *Nat. Genet.*, 12:144–148 (1996); Largaespada, D. A. et al., *Nat. Genet.*, 12:137–143 (1996)), it was surprising that NF1 mutants did not exhibit phenotypic abnormalities associated with excess Ras 1 or Ras 2 activity. Indeed, whereas expression of activated Ras 1 or Ras 2 transgenes results in widespread developmental defects, NF1 mutants are smaller but otherwise patterned normally. The regulation of Ras by NF1 both in vitro and in vivo was therefore examined.

To confirm that Drosophila NF1 can act as a Ras-GAP, GAP assays with bacterial fusion proteins representing the catalytic domains of human p120GAP, and human or Drosophila NF1 were performed. GAP assays were performed as described (Brill, S. et al., *Mol. Cell. Biol.*, 16:4869–4878 (1996), with appropriately diluted lysates of bacteria expressing soluble fusion proteins. Lysates were standardized for total protein content and fusion protein expression level. The human NF1 and p120-GAP catalytic domain fusion proteins were as described (Martin, G. A. et al., *Cell*, 63:843–849 (1990); Martin, G. A. et al., *Science*, 255:192–194 (1992)). The Drosophila NF1 catalytic domain (amino acids 1,235–1,614) was cloned into pGEX20. All three fusion proteins stimulated the GTPase activity of H-Ras, but not of the constitutively active H-Ras$^{va112}$ mutant. Thus, Drosophila NF1 clearly functions as a Ras-GAP in vitro.

RAS 1 function in vivo was then examined. The Drosophila Ras 1 protein performs a crucial function in signaling pathways downstream of several receptor tyrosine kinases (RTKs), including Torso and Sevenless. Since minor perturbations in Ras 1 function have phenotypic consequences in each of these pathways, loss of NF1 perturbations of Torso-controlled specification of embryonic terminal structures or Sevenless-mediated photoreceptor differentiation were examined. The pattern of tailless expression, which is regulated by Torso (Dully, J. B. et al., *Dev. Biol.*, 166:380–395 (1994)), is normal in NF1 deficient embryos. Thus, NF1 does not appear to be an essential regulator of Torso signaling. To test for abnormalities in Sevenless signaling (Simon, M. A. et al., *Cell*, 67:701–716 (1991); Dickson, B. et al., *Curr. Opin. Genet. Dev.*, 4:64–70 (1994); Bonfini, L. et al., *Science*, 255:603–606 (1992)), the retinas of mutant animals were examined. Retinas of NF1$^{P2}$ homozygotes, of NF1'/NF1$^{P1}$ and of NF1$^{P2}$/Df(3R) boss$^{15}$ (17), are completely wild type implying that Ras1-mediated determination of retinal cell fates is unperturbed. This deficiency uncovers the NF1 locus (Hart, A. C. et al., *Genes and Devel.*, 4:1835–1847 (1990)). In homozygotes of NF1$^{P1}$, 25% of ommatidia have one or more extra photoreceptor cells. However, this phenotype may be due to deletion of genes within the neurogenic E(spl) complex, which has occurred in the NF1$^{P1}$ allele. A particularly sensitive indicator of Sevenless pathway function is the sevr$^{E4}$; Sos$^{JC2}$/+ mutant combination. Only approximately 17% of ommatidia in this double mutant have R7 cells, and this number is very sensitive to alterations in the gene dosage of Rasi pathway components (Rogge, R. D. et al., *Cell*, 64:39–48 (1991)). Flies of this genotype which are also heterozygous for NF1$^{P2}$ had no significant alteration in the fraction of R7 containing ommatidia (not shown). Thus, at least two Ras1-mediated signaling pathways downstream of RTKs were not influenced by a reduction in NF1 function.

Although NF1 does not appear to be a major regulator of Ras1 in RTK-mediated signaling, the NF1 deficient phenotype may still reflect improper regulation of other less well characterized functions of Ras1, e.g., in signaling downstream of G-protein-coupled receptors. If so, then manipulating the level or activity of Ras1 pathway components may modify the NF1 deficient phenotype. Loss of function mutants used in this work include: Sos$^{e2H}$, Ras1$^{e1B}$, Ras1$^{e2F}$ (Simon, M. A. et al., *Cell*, 67:701–716 (1991)), and DCO$^{B3}$, Df(2L)Tw2 (Kalderon, D. et al., *Genes Dev.*, 2:1539–56 (1988); Lane, M. E. et al., *Genes Dev.*, 7:1229–43 (1993)). RaP$^{gof}$ is an activated allele of Drosophila Raf((Brand, A. H. et al., *Genes Dev.*, 8:629–639 (1994)). hsp70-PKA* flies harbor a murine PKA transgene with His87Gln and Trp196Arg substitutions that block interaction with the PKA regulatory subunit (Jiang, J. et al., *Cell*, 80:563–572 (1995)). Expression of this gene was induced by daily, 30 minute 37° C. heat shocks or by growing cultures at 25° C. However, heterozygous loss of Ras1 or Sos had no effect on the size of NF1 mutant pupae, nor did crossing in an activated Raf$^{gof}$ mutation. Neither reducing nor increasing signaling through the Ras1-Raf pathway therefore modifies the NF1 phenotype. This raised the possibility that the NF1 mutant phenotype may not involve Ras-Raf mediated signaling.

Example 3

Role of the NF1 Gene Product in the Adenylyl Cyclase-Protein Kinase Pathway

Other workers previously observed that flies carrying a viable heteroallelic combination of mutant alleles of the gene encoding the PKA catalytic subunit, DCO, were reduced in size (Skoulakis, E. M. et al., *Neuron*, 11:197–208 (1993)). For this reason and because an electrophysiological phenotype of NF1 mutants is rescued by cAMP, the cAMP-PKA pathway representing an alternate target for NF1 was tested. Pupae from a heteroallelic combination of DCO mutations (DCO$^{TW2}$/DCO$^{B3}$) were examined and it was found that these are phenotypically indistinguishable from NF1 mutants. Whether increasing PKA activity in NF1 mutant animals would rescue the size defect was then tested. This was achieved by expressing a constitutively active murine PKA catalytic subunit transgene in an NF1 mutant background. Heat shock induced expression of this mutant protein, resulted in lethality. However, lower levels of transgene expression were achieved by growing the cultures at 25° C. Under these conditions, significant rescue of the pupal size defect was consistently observed. In contrast to its effect on NF1 mutant pupae, the PKA transgene did not modify the phenotype of Tubby, a mutation that results in pupae of small size. The dominant Tubby (Tb) mutation maps to 3-90.6, near NF1 (Lindsley, D. L. et al., *The Genetics and Biology of Drosophila melanogaster*, Academic Press, San Diego, 1992). However, 2.9% genetic recombination observed between Tb and the P[w] transposon in the K33 strain indicates that Tb is not an allele of NF1. Nor were wild-type flies expressing the PKA transgene observed to be larger. Since expression of activated PKA suppresses the phenotype of null alleles of NF1, PKA cannot function upstream of NF1 in a simple linear pathway. Therefore, PKA must either function downstream of NF1 or in a parallel pathway.

In addition to their reduced size, NF1 mutants also display a behavioral defect characterized by a diminished escape response. Thus, in an assay that determines the number of flies that escape either spontaneously within 90 seconds of release or after repeated prodding (Richards, S. et al., *Genetics*, 142:1215–1223 (1996)), approximately 15% of either NF1 mutant (n=200) failed to respond, as compared to 3% non-responders for the parental K33 strain. The reduced escape rate does not reflect obvious anatomical defects of the peripheral nervous system or the musculature, and the mutants scored within normal limits in tests measuring their activity or their response to visual or olfactory stimuli (Wehner, R., *J. Insect Physiol.*, 18:1531–1543 (1972); Monte, P. et al., *Behavior Genetics*, 19:267–283 (1989)). Because opening of a post-synaptic K$^+$ channel in the larval neuromuscular junction requires both Ras1 and adenylyl cyclase (Zhong, Y., *Nature*, 375:588–592 (1995)), it seemed possible that aberrant neuromuscular function might explain the diminished escape response. Indeed as described further below, a specific electrophysiological defect was demonstrated at the larval neuromuscular junction, which is rescued by pharmacological manipulation of the cAMP-PKA pathway and is insensitive to manipulation of Ras1-mediated signaling. Therefore, activation of PKA rescues at least two phenotypes associated with loss of NF1.

Example 4

Requirement of Drosophila NF1 Protein for Activation of Adenylyl Cyclase by PACAP38-like Neuropeptides PACAP38-induced responses were recorded by the two-microelectrode voltage-clamp method from body-wall muscle fibers of larvae at the third instar (Zhong, Y., *Nature*, 375:588–592 (1995); Arimura, A. *Regulatory Peptides*, 37:287–303 (1992); Spengler, D. et al., *Nature*, 365:170–175 (1993); Jan, L. Y. et al., *J. Physiol.*, 262:189–214 (1976); Wu, C.-F. et al., *Science*, 220:1076–1078 (1983); Stewart, B. A. et al., *J. Comp. Physiol.*, 175:179–191 (1994)). Electrophysiological recording: The larval body-wall neuromuscular preparation has been described (Zhong, Y. et al., *Neuron*, 14:527–536 (1995); Zhong, Y., *Nature*, 375:588–592 (1995); Jan, L. Y. et al., *J. Physiol.*, 262:189–214 (1976); Wu, C.-F. et al., *Science*, 220:1076–1078 (1983); Stewart, B. A. et al., *J Comp Physiol.*, 175:179–191 (1994)). The setup, saline, recording conditions and voltage paradigms were as described (Zhong, Y. et al., *Neuron*, 14:527–536 (1995); Zhong, Y., *Nature*, 375:588–592 (1995)). For recording the PACAP38-induced synaptic current, the membrane potential was clamped at −80 mV. For recording K$^+$ currents, command voltages were stepped from the holding potential of −80 to −50 and +20 mV, respectively. These currents include outward K$^+$ and inward Ca$^{2+}$ currents, but the inward Ca$^{2+}$ component is completely masked (Singh, S. et al., *Neuron*, 2:1325–1329 (1989)). PACAP38 was applied by pressure ejection through a glass electrode positioned near the voltage-clamped muscle membrane. Forskolin and cAMP analogs were applied to the solution bathing the preparation. Perfusion of PACAP38 to the neuromuscular junction induced an inward current followed by a 100-fold enhancement of K$^+$ currents in wild-type larvae (Zhong, Y. et al., *Neuron*, 14:527–536 (1995); Zhong, Y., *Nature* 375:588–592 (1995)). In NF1$^{P1}$ and NF1$^{P2}$ mutants, the inward current remained mostly intact, but the enhancement of K$^+$ currents was abolished. Because the inward current is not affected in NF1 mutants, it appears that PACAP38 receptors are normally activated by the peptide in these mutants.

To rule out potential developmental effects of the NF1 mutation, transgenic flies carrying an inducible normal NF1 gene were studied. The hsNF1 transgene was expressed after heat shock in transgenic NF1 mutants, hsNF1; NF1 and hsNF1; NF1$^{P2}$. PACAP38-induced enhancement of K$^+$ currents was observed in hsNF1; NF1$^{P1}$ larvae subjected to heat shock (37° C. for 1 hour) and not in those without heat shock. hsNF1; NF1$^{P2}$ larvae, however, showed a normal response to PACAP38 even in larvae not subjected to heat shock. This was probably the result of constitutive expression of the hsNF1 transgene because a large amount of NF1 protein was detected in these flies. To reduce the amount of hsNF1 expression, hsNF1; NF1$^{P2}$/+; NF1$^{P2}$ larvae were selected in which only one copy of the hsNF1 transgene was present. In these larvae, the PACAP38 response was only observed after heat shock. The PACAP38-induced enhancement was fully rescued 4 hours after heat shock, but was observed with a smaller enhancement as early as 1.5 hours after heat shock. Such a time course suggests that all other components in the PACAP38 signaling pathways remain intact so that the preparation resumes PACAP38 responsiveness as soon as enough NF1 protein is synthesized.

Because PACAP38 is a vertebrate peptide (Arimura, A., *Regulatory Peptides*, 37:287–303 (1992); Spengler, D. et al., *Nature*, 365:170–175 (1993)), the response induced by endogenous PACAP38-like neuropeptide was tested (Zhong, Y. et al., *Neuron*, 14:527–536 (1995); Zhong, Y., *Nature*, 375:588–592 (1995)). High frequency stimulation (40 Hz) applied to motor axons through a suction pipette increased K$^+$ currents, presumably by causing release of PACAP38-like peptides (Zhong, Y. et al., *Neuron*, 14:527–536 (1995)). This evoked PACAP38-like response was also eliminated in NF1 mutants and rescued by the expression of the hsNF1 transgene.

Because the NF1 protein acts as a Ras-GAP (Xu, G. F. et al., *Cell*, 62:599–608 (1990); Xu, G. F. et al., *Cell*, 63:835–841 (1990); Buchberg, A. M. et al., *Nature*, 347:291–294 (1990); Ballester, R. et al., *Cell*, 63:851–859 (1990); Martin, G. A. et al., *Cell*, 63:843–849 (1990)), two null alleles of Drosophila Gap1, rI$^{533B1}$ and rI$^{533PB}$ were examined. Flies carrying the mutations have disrupted eye development that results from increased Ras activity (Gaul, U. et al., *Cell*, 68:1007–1019 (1992)). PACAP38 induced a normal enhancement of $K^+$ currents in both Gap1 mutants. Moreover, recordings from transgenic larvae showed that induced expression of constitutively active Ras (Ras$^{V12}$) (Fortini, M. E. et al., *Nature*, 355:559–561 (1992)) or active Raf protein kinase (Raf$^{gof}$) (Brand, A. H. et al., *Genes & Development*, 8:629–639 (1994)) neither blocked nor mimicked the PACAP38 response (Zhong, Y., *Nature*, 375:588–592 (1995)). These results suggest that failure to negatively regulate Ras-Raf signaling does not explain the defective PACAP38 response in NF1 mutants.

Application of the membrane permeable cAMP analogs, dibutyryl cAMP or 8-bromo cAMP to the larval neuromuscular preparation is insufficient to produce the PACAP38-like enhancement of $K^+$ currents (Zhong, Y., *Nature*, 375:588–592 (1995); Zhong, Y. et al., *J. Neurogenet.*, 9:15–27 (1993)) and appeared not to disrupt the PACAP38 response in wild-type larvae. This implies that cAMP may not cause inhibition of the Raf activity as reported in other preparations (Cook, S. J. et al., *Science*, 262:1069–1072 (1993)). Application of these cAMP analogs to NF1 mutants did restore the normal response to PACAP38. Both NF1$^{P2}$ homozygotes and heteroallelic NF1$^{P1}$/NF1$^{P2}$ larvae showed enhanced $K^+$ currents. NF1$^{P1}$ larvae also responded, but with a smaller amplitude of response, which may be a non-specific effect of genetic background because the response of NF1$^{P1}$/NF1$^{P2}$ heterozygotes to PACAP38 was fully restored by treatment with cAMP analogs.

The cAMP analogs were effective if applied any time before or within 2 min. after applying PACAP38. After 2 minutes, cAMP analogs failed to enhance the response of NF1$^{P2}$ mutants to PACAP38. This time course is consistent with a model whereby in NF1 mutants, the Ras-Raf pathway is normally activated in response to PACAP38 for 2 rnin, but the cAMP pathway is blocked. Therefore, synergistic modulation of $K^+$ currents can be achieved if cAMP analogs are supplied during the transient activation of the Ras-Raf pathway. Addition of cAMP analogs also restored the response to PACAP38 in rut$^1$ mutants, but not in Ras$^{120}$ mutants (Livingstone, M. S. et al., *Cell*, 37.205–215 (1984); Levin, L. R. et al., *Cell*, 68:479–489 (1992); Zhong, Y., *Nature*, 375:588–592 (1995)).

To further test whether activation of cAMP signaling rescues the defective PACAP response of NF1 mutants, the drug forskolin, which stimulates G-protein coupled adenylyl cyclase activity (Seamon, K. B. et al., *J. Cyclic Nucleotide Res.*, 7:201–224 (1981); Dudai, Y. et al., *J. Neurogenet.*, 2:365–380 (1985)), was applied to the neuromuscular preparation. PACAP38 induced a normal response in NF1$^{P2}$ and NF1$^{P1}$/NF1$^{P2}$ mutants exposed to forskolin. This indicates that adenylyl cyclase is present, but is not activated by receptors for PACAP38-like neuropeptides. Forskolin also restored the PACAP38 response in rut$^1$ mutants even though the Rut-adenylyl cyclase is completely nonfimctional (Livingstone, M. S. et al., *Cell*, 37:205–215 (1984); Levin, L. R. et al., *Cell*, 68:479–489 (1992)). It is possible that cAMP synthesized by other adenylyl cyclases upon forskolin stimulation is sufficient to modulate $K^+$ currents together with the Ras pathway activated by PACAP38 (Livingstone, M. S. *Proc Natl Acad Sci USA*, 82:5992–5996 (1985)).

Adenylyl cyclase shows abnormal subcellular localization in yeast IRA mutants (Mitts, M. R. et al., *Mol. Cell Biol.*, 11:4591–4598 (1991)). The IRA gene encodes proteins that are distantly related to the NF1 protein and that are involved in mediating Ras-dependent activation of adenylyl cyclase. Although the yeast cyclase is very different from Rut-adenylyl cyclase and other cyclases in higher organisms (Toda, T. et al., *Cell*, 40:27–36 (1985); Tanaka, K. et al., *Cell*, 60:803–807 (1990)), adenylyl cyclase activity in membrane fractions was examined. Adenylyl cyclase activity was assayed as described (Livingstone, M. S. et al., *Cell*, 37:205–215 (1984)) with membranes from abdomens of rut$^1$, NF1$^{P2}$, and wild type flies. Calcium concentrations were calculated according to MaxChelator v1.31 (Bers, D. M. et al., *Methods Cell. Biol.*, 40:3–29 (1994)). Assays were done in duplicate and each result represents data from at least two eparate experiments. The Rut-adenylyl cyclase is the only cyclase that can be activated by $Ca^{2+}$-calmodulin (CaM) in the tissues from fly abdomen, as indicated by the lack of the $Ca^{2+}$-dependent cyclase activity in rut$^1$ mutants (Livingstone, M. S. et al., *Cell*, 37:205–215 (1984); Levin, L. R. et al., *Cell*, 68:479–489 (1992)). In addition, the basal activity (Livingstone, M. S. et al., *Cell*, 37:205–215 (1984)) and the forskolin-stimulated (Dudai, Y. et al., *J. Neurogenet.*, 2:365–380 (1985)) activity of adenylyl cyclase were also reduced in rut$^1$mutants. However, NF1 mutations did not affect the basal activity, the $Ca^{2+}$-dependent activity, or the forskolin-stimulated activity of adenylyl cyclase. Therefore, Rut-adenylyl cyclase is present in these membranes and can be normally activated by $Ca^{2+}$-CaM and forskolin.

The following materials and methods were used in the work described in Examples 5, 6 and 7.

Fly Stocks

NF1$^{P1}$, NF1$^{P2}$ and K33 flies have a similar genetic background. These flies were outcrossed with w$^{1118}$ (isoCJ1), an isogenic line (Yin, J. C. P. et al., *Cell*, 79:49–58 (1994)), for five generations. Thus, NF1$^{P1u}$, NF1$^{P2u}$ and K33$^u$ have a genetic background similar to w$^{1118}$ (isoCJ1).

As described above, the transgenic hsNF1 gene is inserted in the second chromosome. In all experiments related to hsNF1, only heterozygous hsNF1/+ was used which avoided any recessive effects of the insertion on behavior.

hsp 70-PKA* flies have a murine PKA transgene, with His87Gln and Trp196Arg substitutions that prevent interaction with the PKA regulatory subunit (Jiang, J. and Struhi, G., *Cell*, 80:563–572 (1995)).

Pavlovian Learning

Flies were trained by exposure to electroshock (12 pulses at 60 V, duration of 1.5 seconds, interval of 5 seconds) paired with one odour (benzaldehyde (BA, 4%) or methylcyclohexanol (MCH, 10°) for 60 seconds) and subsequent exposure to a second odour without electroshock. The odour concentrations were adjusted to assume no preference for flies exposed simultaneously to the two odours before the training. Immediately after training, learning was measured by allowing flies to choose between the two odours used during training. No preference between odours results in zero (no learning) performance index (PI). Avoidance of the odour previously paired with electroshock produces a $0<PI\leq1.00$ (see Tully, T. and Quinn, W. G., *J. Comp. Physiol. A Sens. Neural. Behav. Physiol.*, 157:263–277 (1985)).

Olfactory Acuity

Absolute odour avoidance responses were quantified by exposing naïve to each odour (BA or MCH) or air in the T-maze. After 120 seconds, the numbers of flies in each arm of the T-maze were counted, and performance index was calculated for each odour individually as described in Dura, J.-M. et al., *J. Neurogenetics*, 9:1–14 (1993).

Shock Reactivity

The ability to sense and escape from electric shock was quantified by inserting electrifiable grids into both arms of the T-maze, and delivering shock pulses to one arm. Flies were transported to the choice point of the T-maze, where they could choose between the two arms. After 60 seconds, the center compartment was closed, trapping flies in their respective arms. Individual PI was calculated as defined (Dura, J.-M. et al., *J. Neurogenetics*, 9:1–14 (1993)).

Adenylyl Cyclase Activity Assay

The adenylyl cyclase activity assay described in Livingstone, M. S., *Proc. Natl. Acad. Sci. USA*, 82:5992–5996 (1985)) was modified as follows. The membrane fraction was extracted from either male heads with the cuticle removed to leave essentially brain tissue, or from 10 male abdomens. Twenty (20) dissected brains in 850 µl lysis buffer were homogenized, and the membrane fraction was extracted by centrifugation at 178,000 g for 10 minutes. GTPγS (final concentration, 20 µM) was added to stimulate G-protein activated adenylyl cyclase activity immediately after homogenization but before centrifugation. When assaying the basal level of adenylyl cyclase activity, GTPγS was not added. These modifications seemed to amplify the NF1 effect. Calcium concentrations were calculated according to MaxChelator v1.31 (Bers, D. M. et al., *Methods. Cell. Biol.*, 40:3–29 (1994)).

RT-PCR of Induced NF1 Expression

Total RNA was prepared from 100 mg flies using the RNeasy Mini Kit (Qiagen). Messenger RNA was isolated from total RNA (20–100 µg) by using either the Dynabeads mRNA DIRECT Micro Kit or the Dynabeads mRNA Purification Kit (Dynal) and first strand complementary DNA was synthesized directly from this mRNA using the SuperScript Prearnplification System (Gibco BRL). PCR amplification with Taq DNA polymerase (Gibco BRL) was carried out in the manufacturer's buffer using 1.5 mM $MgCl_2$ with 30 cycles of 94° C. for 1 minute, 55° C. for 1 minute, 72° C. for 1 minute, followed by extension at 72° C. for 10 minute. NF1-specific primers, 5'-tcaccaaagctcagagcacga-3' (SEQ ID NO:3) and 5'-gccttgttgcaggatttgagt-3' (SEQ ID NO:4), were designed to amplify a 1,251 bp region of the cDNA between bases 2,730 and 3,981 (Genbank L2650 1). These primers span a region of genomic DNA containing a 54-bp intron that allows distinction between cDNA products and potential genomic contaminants. Lack of genomic DNA contamination was confirmed by the absence of any PCR products when RT-PCR was carried out in control reactions without reverse transcriptase. Ribosomal protein rp49-specific primers, 5'-atgaccatccgcccagcatac-3' (SEQ ID NO:5) and 5'-gagaacgcaggcgaccgttgg-3' (SEQ ID NO:6), were designed to amplify a 391-bp fragment between bases 1 and 391 of the rp49 coding region (Genbank Y13939) (O'Connell, P. and Rosbash, M., *Nucleic Acids Res.*, 12:5495–5513 (1984)). The control rp49 mRNA should be expressed at equal levels in all cells at all stages (O'Connell, P. and Rosbash, M., *Nucleic Acids Res.*, 12:5495–5513 (1984)).

Example 5

Olfactory Associative Learning, Shock Reactivity and Odour Avoidance

Figure 3A:
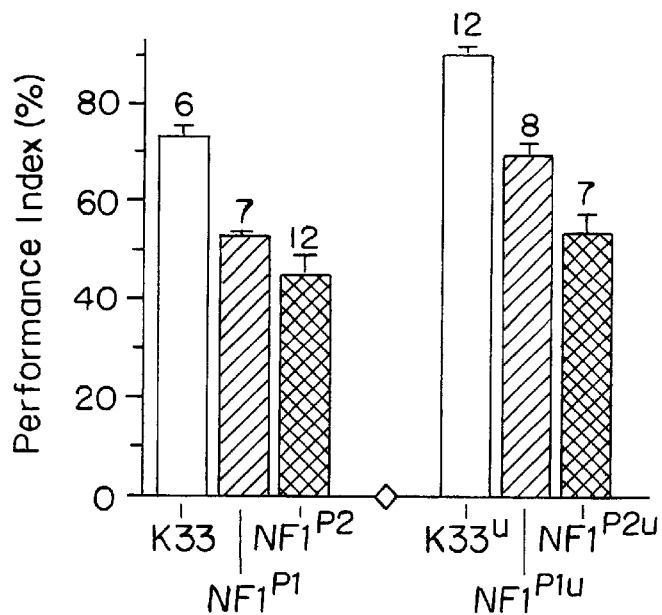
FIG. 3A is a bar graph representation of results showing the NF1 learning defects observed in both the original and outcrossed isogenic (marked by u in superscript) genetic background. K33=control flies (parental line for NF1 mutant flies; wildtype); NF1$^{P1}$=NF1 mutant flies; NF1$^{P2}$=NF1 mutant flies; K33$^u$=control flies K33 flies outcrossed with isogenic line w$^{118}$); NF1$^{P1u}$=NF1 mutant flies (NF1$^{P1}$ outcrossed with isogenic line w$^{1118}$); NF1$^{P2u}$=NF1 mutant flies (NFP1$^{P2}$ outcrossed with isogenic line w$^{1118}$). The number of assays for each group is indicated above each error bar.

Olfactory associative learing of adult fruit flies was examined using a well-defined Pavlovian procedure (Tully, T. and Quinn, W. G., *J. Comp. Physiol. A Sens. Neural. Behav. Physiol.*, 157:263–277 (1985); de Belle, J. S. and Heisenberg, M., *Science*, 263:692–695 (1994); Connolly, J. B. et al., *Science*, 274:2104–2106 (1996); and Grotewiel, M. S. et al., *Nature*, 391:455–460 (1998)). Significant decrements in olfactory learning performance were shown for two independently isolated NF1 null alleles, $NF1^{P1}$ and $NF1^{P2}$, as compared with K33, the parental line for NF1 mutants with a P-element inserted nearby the NF1 locus (Table 1 and FIG. 3A).

TABLE 1

Performance Indice for Olfactory Learning, Shock Reactivity and Odour Avoidance

| Genotypes[1] | Learning (n) | Shock Reactivity | | Odour Avoidance | | | |
|---|---|---|---|---|---|---|---|
| | | | | BA Dilution | | MCH Dilution | |
| | | 60 V | 20 V | 4% | 0.4% | $10^0$ | $10^{-1}$ |
| K33 | 73 ± 2(6) | 72 ± 6 | 25 ± 9 | 78 ± 5 | 28 ± 10 | 73 ± 7 | 40 ± 9 |
| $NF1^{P1}$ | 53 ± 1(7)* | 77 ± 4 | 30 ± 5 | 80 ± 3 | 25 ± 4 | 66 ± 8 | 36 ± 6 |
| $NF1^{P2}$ | 45 ± 4(12)* | 76 ± 3 | 26 ± 5 | 71 ± 4 | 19 ± 6 | 67 ± 4 | 29 ± 7 |
| hsNF1/+; $NF1^{P2}$ | 75 ± 2(4) | 65 ± 3 | 23 ± 6 | 79 ± 6 | 32 ± 11 | 83 ± 4 | 34 ± 7 |
| $K33^u$ | 90 ± 1(12) | 89 ± 2 | 61 ± 6 | 92 ± 1 | 41 ± 8 | 77 ± 5 | 63 ± 5 |
| $NF1^{P1u}$ | 70 ± 2(8) | 80 ± 5 | 56 ± 8 | 85 ± 5 | 36 ± 9 | 84 ± 6 | 59 ± 8 |
| $NF1^{P2u}$ | 54 ± 4(7)* | 83 ± 3 | 62 ± 7 | 93 ± 2 | 41 ± 7 | 77 ± 4 | 58 ± 5 |

[1]K33, $NF1^{P1}$, $NF1^{P2}$ and hsNF1/+; $NF1^{P2}$ have a similar genetic background, whereas $K33^u$, $NF1^{P1u}$ and $NF1^{P2u}$ have a different background. All scores are expressed as PI ± SEM. For learning, the number (n) of assays are indicated in parentheses. For all shock reactivity and odour avoidance assays, N = 8.
*Statistically different from control. No statistical difference at the level of α = 0.05 is detected among all the sensorimotor activities. Learning defect is significant at α ≦ 0.001. Comparison is made between mutants and controls with the similar genetic background using Tukey-Kramer HSD test within the Macintosh software package JMP3.1 (SAS Institute, Inc., Cary, NC).

Olfactory avoidance and electric-shock reactivity (Dura, J.-M. et al., *J. Neurogenetics*, 9:1–14 (1993)), two sensorimotor activities necessary for performing the learning task, were similar in the mutant and control K33 flies (Table 1).

To consider the potential effects of genetic background on behavior (Dura, J.-M. et al., *J. Neurogenetics*, 9:1–14 (1993)), NF1 mutants and K33 were outcrossed with an isogenic line $w^{1118}$ (isoCJ1) (Yin, J. C. P. et al., *Cell*, 79:49–58 (1994)). Again, learning scores of NF1 mutants were significantly reduced (Table 1 and FIG. 3A), whereas the parameters of sensorimotor activities were not statistically different from the control with a similar genetic background (Table 1). Even though learning scores and some scores for shock reactivity and odour avoidance are significantly different for K33 in different genetic backgrounds, these behavioral parameters also vary accordingly in NF1 mutants (Table 1). These results indicate that NF1 is a learning mutant. This conclusion is further supported by the observation that the learning defect was rescued by induced expression of the NF1 transgene (see below) without changing sensorimotor activity significantly (Table 1).

Figure 3B:
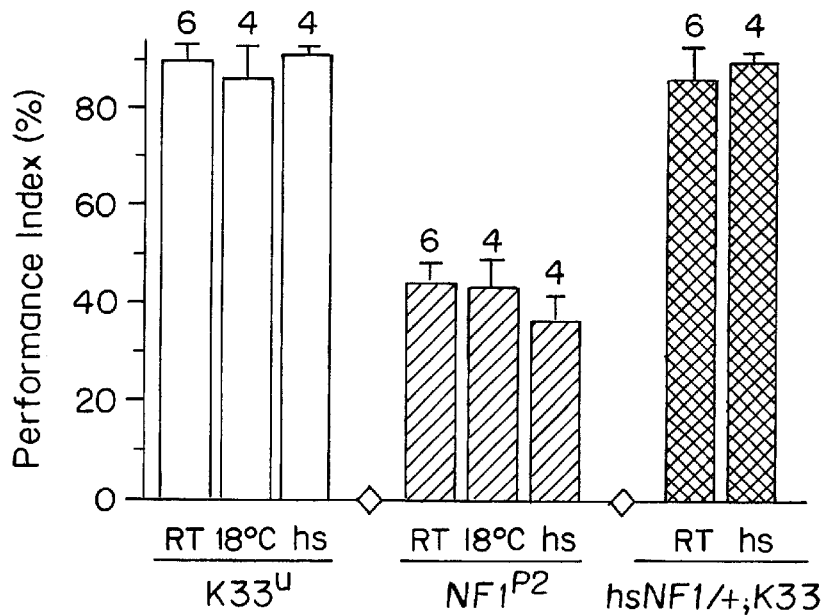
FIG. 3B is a bar graph representation of results showing the effect of heat shock induction on learning scores in K33$^u$, NF1$^{P2}$ and hsNF1/+; K33 flies. K33$^u$=control flies; NF1$^{P2}$= NF1 mutant flies; hsNF1/+; K33=heterozygous transgenic NF1 flies; hs=heat shock. The number of assays for each group is indicated above each error bar.

The effect of heat-shock induced expression of the NF1 transgene was examined to determine whether the learning defect is caused by an adult requirement for NF1 or whether the learning defect is a secondary consequence of developmental abnormalities, such as the small body size of NF1 mutants. Heat-shock treatment of hsNF1 transgenic flies leads to expression of the NF1 protein. Such treatment did not affect learning scores in NF1 mutants, control flies and hsNF1; K33 (FIG. 3B). However, learning scores were improved when mutant flies carrying the NF1 transgene were heat shocked.

Figure 3C:
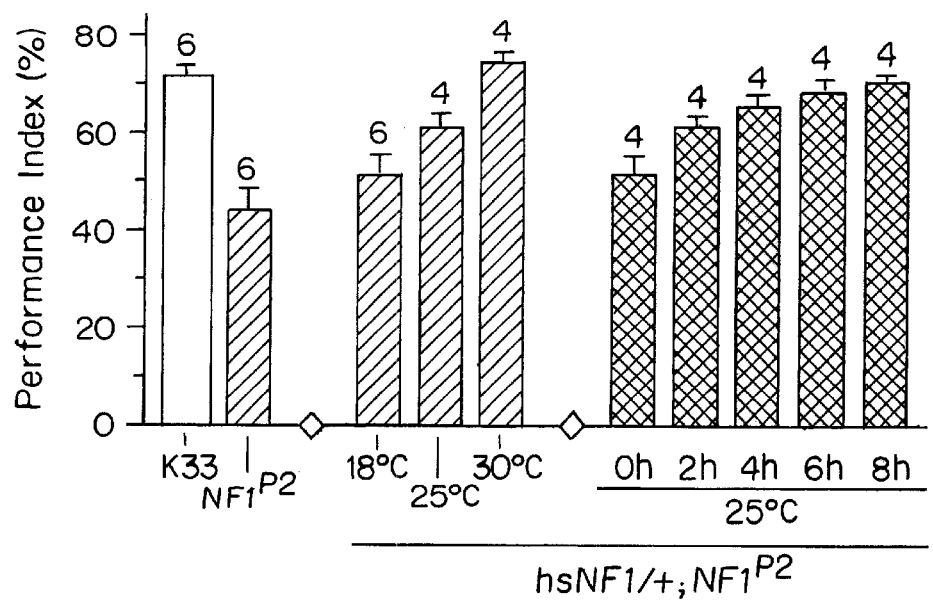
FIG. 3C is a bar graph representation of results showing rescue of the NF1 learning defect by induced expression of the NF1 transgene. K33=control flies; NF1$^{P2}$=NF1 mutant flies; hsNF1/+; NF1$^{P2}$=heterozygous transgenic NF1 flies; hs=heat shock. The number of assays for each group is indicated above each error bar.

Heterozygous transgenic NF1 (hsNF1/+; $NF1^{P2}$) flies were raised at room temperature (RT, 20–24° C.). These flies showed a learning score PI of 63±3 (n=5), indicating a partial rescue because of leaky expression. To minimize the leaky expression of the heat-shock promoter-controlled NF1 transgene, flies were shifted to 18° C. overnight before the test. This reduced the learning score significantly to 52±4 (FIG. 3C). Learning scores of transgenic flies (hsNF1/+; $NF1^{P2}$ were improved to a better extent when flies were treated at 30° C. as compared with 25° C. for two hours (P<0.05, Tukey Kramer HSD) (FIG. 3C) or when the transgenic flies were subjected to 25° C. for successively longer times (i.e., for 0, 2, 4, 6 or 8 hours, respectively) (significant for 2 hours, P<0.05) (FIG. 3C). Presumably, more NF1 was expressed with higher temperatures or for longer times of treatment.

This is supported by data from semi-quantitative polymerase chain reaction with reverse transcriptase (RT-PCR), which showed induced expression of the hsNF1 transgene. RT-PCR was performed using NF1-specific primers with complementary DNA (cDNA) prepared from hsNF1; $NF1^{P2}$ flies grown at 18° C., 25° C. and 30° C. or given daily 1 hour heat shock at 37° C., or from $NF1^{P1}$ mutant flies or K33 wild type flies grown at 18° C. Control RT-PCR was performed from the same cDNA using ribosomal protein rp49-specific primers. Higher temperature treatment led to accumulation of more messenger RNA (mRNA) transcribed from the hsNF1 transgene. Three separate mRNA isolations showed the same pattern of increased expression of the hsNF1 transgene at increased temperature. Thus, the level of performance improvement may be proportional to the amount of NF1 expressed.

A single heat-shock treatment during larval stages did not change the smaller body size of NF1 mutants, quantified by measuring the length of pupal cases. hsNF1/+; $NF1^{P2}$ pupal cases (2.73±0.14; n=66) were indistinguishable after treatment from $NF1^{P2}$ (2.69±0.2; n=56), but were smaller than those of control K33 (3.2±0.13; n=70). Repetitive or continuous heat-shock treatments, however, rescue the developmental phenotype. Thus, the learning defect can be rescued by acute expression of the NF1 transgene during adulthood, but the developmental defect requires repetitive or continuous heat-shock treatment during development. This suggests that NF1 is essential for the learning process.

Example 6

Effect of the cAMP Pathway on NF1-Dependent Learning and Memory

Figure 4A:
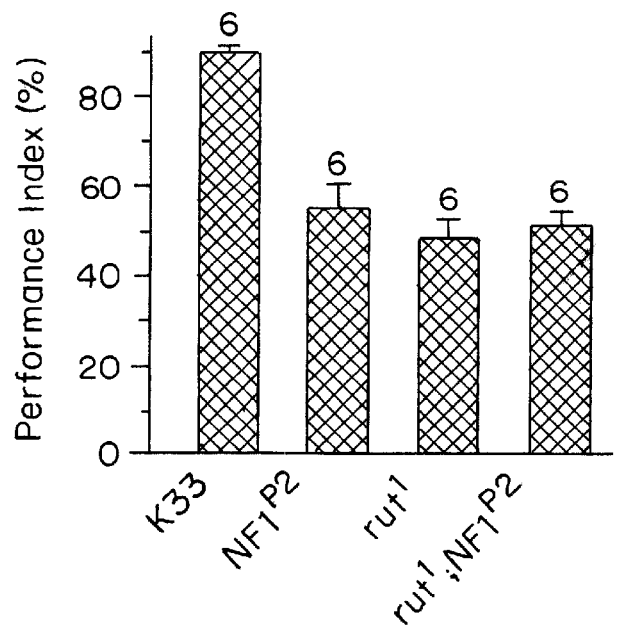
FIG. 4A is a bar graph representation of results comparing the learning scores of NF1$^{P2}$ and rut$^1$ single-mutant flies and rut$^1$; NF1$^{P2}$ double-mutant flies. K3=control flies; NF1$^{P2}$= NF1 mutant flies; rut$^1$=rutabaga mutant flies; rut$^1$; NF1$^{P2}$= rutabaga and NF1 double mutant flies.

To test whether the NF1-dependent learning defect involves the cAMP pathway, learning scores of $NF1^{P2}$ and $rut^1$ single-mutant, and $rut^1$; $NF1^{P2}$ double-mutant flies were compared. The learning scores of all three mutant genotypes were very similar (FIG. 4A). The learning score of another double mutant, dunce (dnc); $rut^1$ is reduced when compared with either single mutants (Tully, T. and Quinn, W. G., *J. Comp. Physiol. A Sens. Neural. Behav. Physiol.*, 157:263–277 (1985)), which indicates that the two mutations exert additive effects on learning even though both gene products are involved in the cAMP cascade (Rut-adenylyl cyclase (AC) for synthesizing cAMP (Livingstone, M. S. et al., *Cell*, 37:205–215 (1984); and Levin, L. R. et al., *Cell*, 68:479–489 (1992)) and Dnc-phosphodiesterase for degrading cAMP (Byers, D. et al., *Nature*, 289:79–81 (1981); and Chen, C. N. et al., *Proc. Natl. Acad. Sci. USA*, 86:3599–3603 (1986)). Therefore, the absence of any further reduction of learning in the double mutant $rut^1$; $NF1^{P2}$ suggests that both gene products function closely in the cAMP pathway.

Figure 4B:
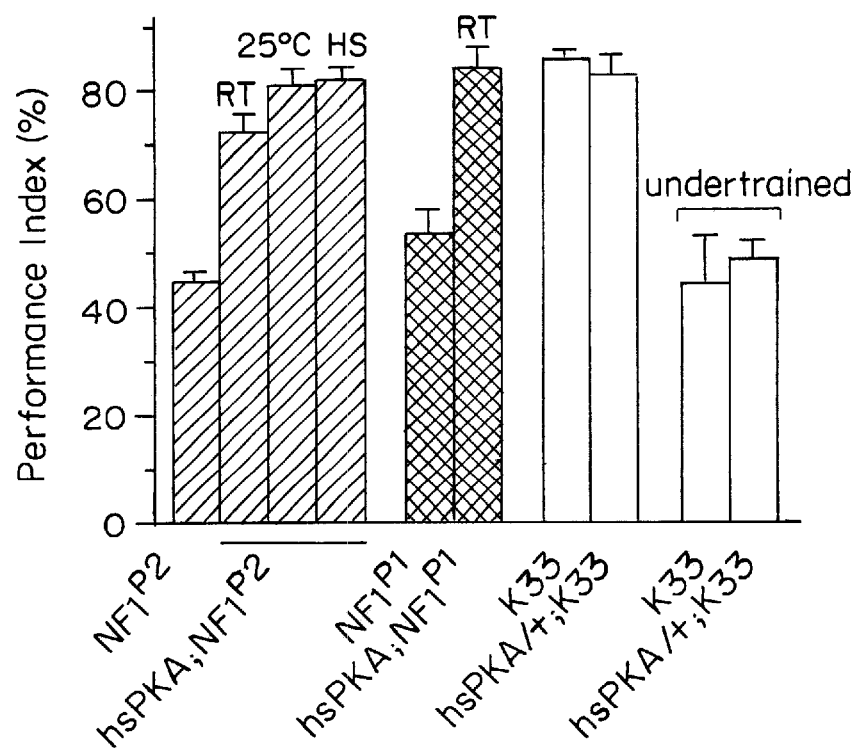
FIG. 4B is a bar graph representation of results showing rescue of NF1 learning defects by induced expression of a constitutively active catalytic subunit of cAMP-dependent protein kinase (PKA*). NF1$^{P1}$ and NF1$^{P2}$=NF1 mutant flies; hsPKA; NF1$^{P1}$ and hsPKA; NF1$^{P2}$=NF1 mutant flies carrying a transgene encoding the PKA* subunit; K33=control flies; hsPKA/+; K33=K33 flies carrying a transgene encoding the PKA* subunit; hs=heat shock. From left to right, n=6, 6, 6, 5, 4, 6, 6, 6, 4, 4.

This is supported by studies of NF1 mutant flies carrying a transgene encoding a mutant catalytic subunit of cAMP-dependent protein kinase (PKA*), which is constitutively active (Jiang, J. and Stuhl, G., *Cell*, 80:563–572 (1995)). As discussed above, sustained expression of this PKA subunit rescues the small body size phenotype of NF1 mutants. Heat shock induction of the constitutively active PKA should, in principle, bypass the requirement for the Rut-AC and all other molecules upstream of normal PKA activation. The hsp70-PKA* transgene completely rescued the learning defect of $NF1^{P1}$ when the flies were raised at RT (FIG. 4B). $NF1^{P2}$ mutants were partially rescued by the transgene at RT, but showed complete rescue with heat shock (37° C., 30 minutes), or with a shift to 25° C. overnight before being tested (FIG. 4B). In addition, it was found that NF1 mutations also caused a short-term memory defect (3- and 8-hour retention, FIG. 4C; $NF1^{P1}$ not shown), which was also filly rescued by heat shock induction of PKA*. To determine whether expression of hsp70-PKA* induces a non-specific enhancement of learning, it was shown that leaky or induced expression of hsp-PKA* in the wild-type background did not increase the learning score even if flies were under-trained (FIG. 4B). For undertraining, flies were subjected to three (3) repeats of electric shock in a training trail instead of 12 to avoid any ceiling effect on learning scores (see above and Tully, T. and Quinn, W. G., *J. Comp. Physiol. A Sens. Neural. Behav. Physiol.*, 157:263–277 (1985)). The learning scores were reduced in K33 and hsPKA*/+; K33 in parallel. Heat shock was at 37° C. for 30 minutes and training started after a 3-hour rest. Flies were shifted to 25° C. overnight before training (25° C.).

Based on these results, it was concluded that the PKA* effect is not non-specific and that the learning defect observed in NF1 mutants can be rescued by induction of PKA activity. Therefore, the biochemical deficiency in the NF1 mutants must reside upstream of PKA induction in the cAMP pathway.

Figure 4C:
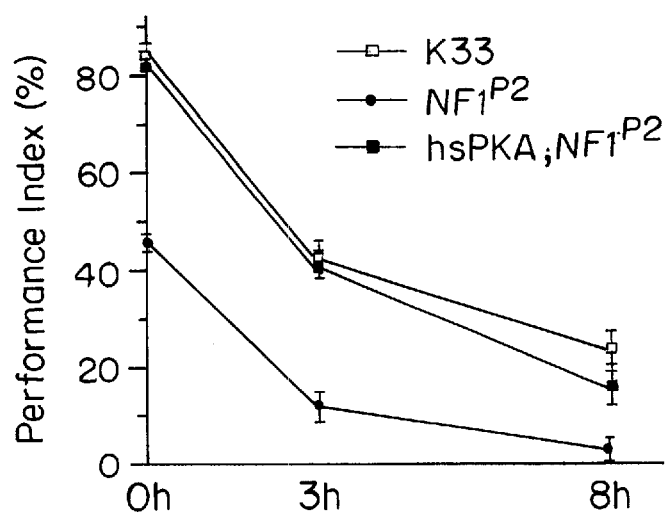
FIG. 4C is a graphic representation of results showing rescue of short-term memory defect by induced expression of the PKA* subunit. K33=control flies; NF1$^{P2}$=NF1 mutant flies; hsPKA; NF1$^{P2}$=NF1 mutant flies carrying a transgene encoding the PKA* subunit; hs=heat shock. n=6–12.

Retention at 3 and 8 hours after training was also disrupted in NF1 mutants (FIG. 4C). This short term memory defect was rescued by induced expression of the PKA* subunit. Flies were raised at RT and heat shocked for 30 minutes at 37° C. and then rested for at least 3 hours before training.

Example 7

Effect of NF1 on Adenylyl Cyclase Activity

Figure 5A:
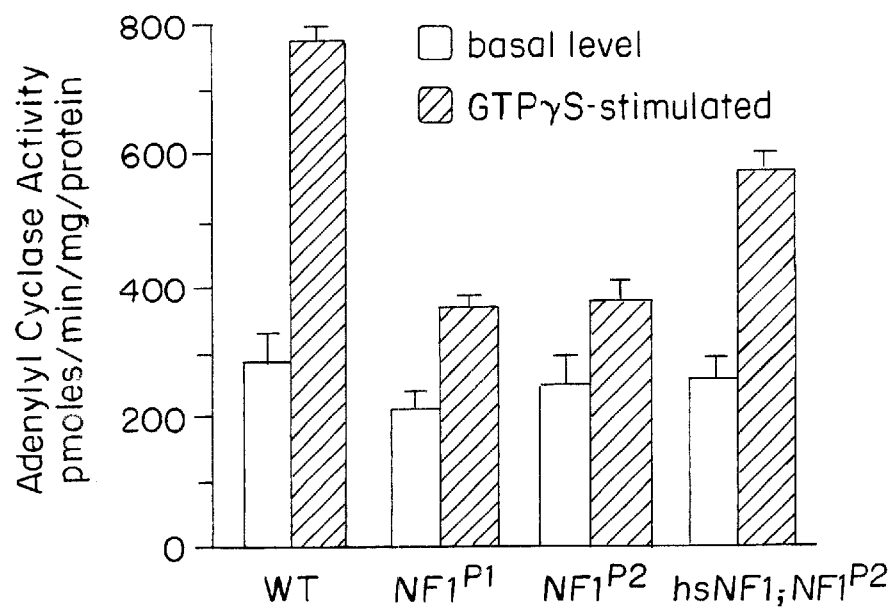
FIGS. 5A and 5B are bar graph representations showing the results of biochemical assays of the effect of NF1 on GTPγS-stimulated adenylyl cyclase activity in brain tissues. WT=wildtype (K33); NF1$^{P1}$ and NF1$^{P2}$=NF1 mutants; hsNF1; NF1$^{P2}$=heterozygous transgenic NF1 flies; rutabaga=rutabaga mutant; rutabaga; NF1$^{P2}$=rutabaga and NF1 double mutant flies. For FIG. 5A, each data point (mean±SEM) is the average of 4 independent experiments. For FIG. 5B, data points are the average of 3 independent experiments.

The behavioral analyses described above corroborate the electrophysiological data that indicated that NF1 might exert its effect through regulation of the activation of Rut-AC. Biochemical assays provide direct evidence to support the electrophysiological data. Previous experiments have shown that Rut-AC expressed in a cell line can be stimulated not only by $Ca^{2+}$/calmodulin, but also by reagents that stimulate G-proteins, including GTPγS and $AIF_4^-$ (see Levin, L. R. et al., Cell, 68:479–489 (1992)). First, AC activity in membrane fractions of adult brain tissues was examined. To be comparable, all flies were subjected to heat shock (for 2 hours at 35° C. and 1 hour rest at RT). The basal level of AC activity was very similar in the control (K33) and NF mutant membranes, but the GTPγS stimulated AC activity was markedly reduced in $NF1^{P1}$ and $NF1^{P2}$ mutant membranes (FIG. 5A). However, significant GTPγS-stimulated activity occurred above the basal level in the mutants. Overexpression of NF1 in control flies did not increase AC activity, whereas the reduction in stimulated AC activity seen in NF1 mutants was mostly rescued by acutely induced expression of the NF1 transgene (FIG. 5A), indicating that NF1 is indeed able to regulate cAMP synthesis. Thus, GTPγS-stimulated AC activity consists of two components: one that is NF1-dependent and one that is NF1-independent.

Figure 5B:
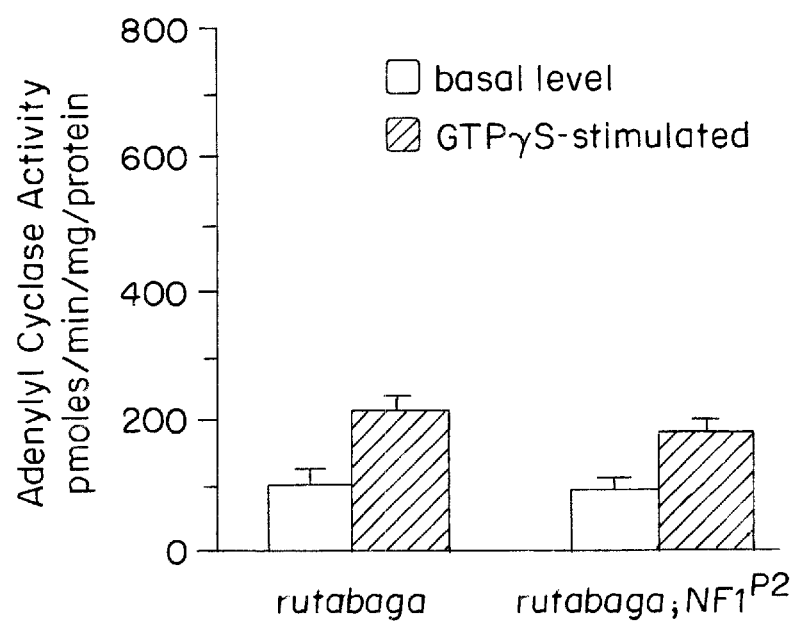

To determine whether the NF1-dependent AC activity is due to Rutabaga, $rut^1$ and $rut^1$; $NF1^{P2}$ mutant flies were assayed. To be comparable, all flies were subjected to heat shock (for 2 hours at 35° C. and 1 hour rest at RT). AC activity in membrane fractions of adult brain tissues was examined. The basal and GTPγS-stimulated level of AC activity were very similar in the single mutant, $rut^1$, and in the double mutant, $rut^1$; $NF1^{P2}$ (FIG. 5B). Thus, the NF1 mutation has no impact on AC activity in the absence of Rut-AC. In other words, the NF1-dependent cAMP activity is mediated through Rut-AC. There is a diminished NF1 effect on AC activity in the rut mutant background.

Figure 5C:
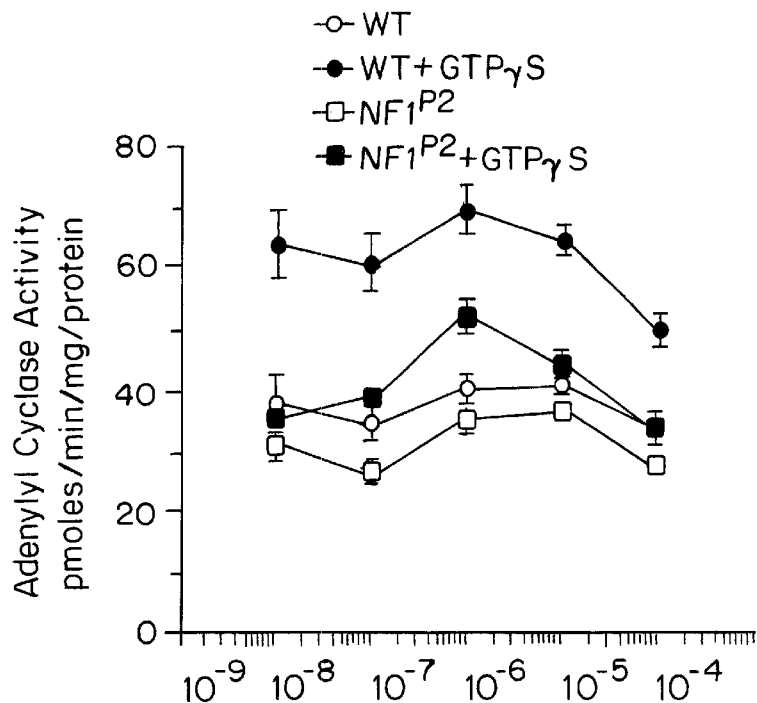
FIGS. 5C and 5D are graphic representations showing the results of biochemical assays of the effect of NF1 on Ca$^{2+}$-dependence of adenylyl cyclase activity in abdominal tissues. WT=wildtype (K33); NF1$^{P2}$=NF1 mutant; rutabaga=rutabaga mutant; rutabaga; NF1$^{P2}$=rutabaga and NF1 double mutant flies; +GTPγS=GTPγS-stimulated adenylyl cyclase activity. For FIG. 5C, the average of 8 independent experiments is shown. For FIG. 5D, the average of 6 independent experiments is shown.
Figure 5D:
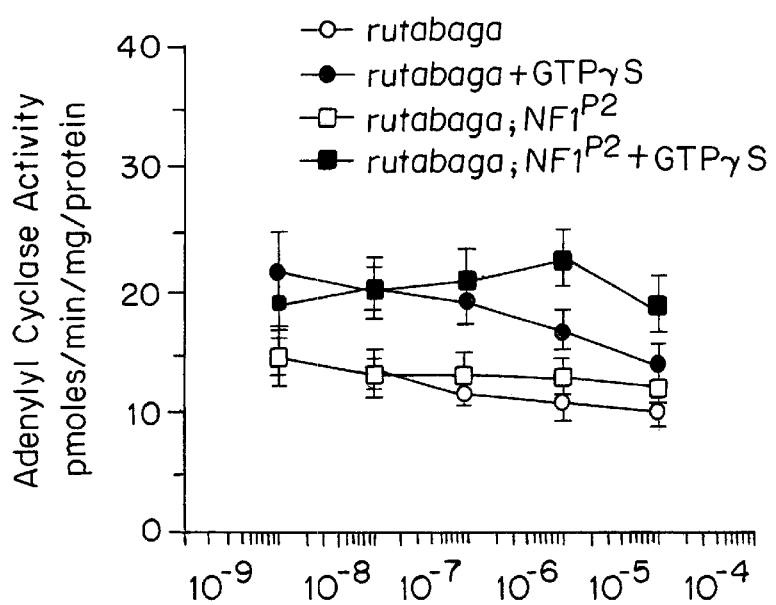

The $Ca^{2+}$-dependence of the NF1 effect was measured to determine how Rut-AC is involved. Membrane fractions extracted from abdominal tissues were used because the $Ca^{2+}$-dependent Rut-AC activity is easier to detect (FIGS. 5C and 5D). The data described herein are consistent with a previous report (Livingstone, M. S. et al., Cell, 37:205–215 (1984)) that the $Ca^{2+}$-dependent peak of AC activity is missing in rut mutants. Again, the NF1 mutation had no significant effects on AC activity across $Ca^{2+}$ concentrations without Rut-AC (FIG. 5D). Moreover, the $Ca^{2+}$-dependent peak of Rut-AC activity was dependent upon G-protein stimulation, but not the presence of NF1 (FIG. 5C).

The teachings of all the articles, patents and patent applications cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for screening a pharmaceutical agent for its ability to treat a short term memory defect in an animal, wherein the short term memory defect is associated with a defect in the Neurofibromatosis 1 protein, comprising:

a) administering said pharmaceutical agent to an animal with a short term memory defect associated with a defect in the Neurofibromatosis 1 protein;

b) training said animal treated in step a) under conditions appropriate to produce short term memory formation in said animal;

c) assessing short term memory formation in said animal trained in step b); and d) comparing short term memory formation assessed in step c) with short term memory formation produced by the training protocol of step b) in a control animal to which said pharmaceutical agent has not been administered, wherein the pharmaceutical agent is identified as one having the ability to treat said short term memory defect in said animal if short term memory formation assessed in step c) is greater than short term memory formation produced in said control animal.

2. The method of claim 1 wherein said animal is a mammal.

3. The method of claim 1 wherein said animal is a Drosophila species.

4. The method of claim 2 wherein said animal is a rodent.

5. A method for screening a pharmaceutical agent for its ability to treat a learning defect in an animal, wherein the defect is associated with a defect in the Neurofibromatosis 1 protein, comprising:

a) administering said pharmaceutical agent to an animal with a learning defect associated with a defect in the Neurofibromatosis 1 protein; and b) training said animal treated in step a) under conditions appropriate for learning by said animal;

c) assessing learning ability by said animal trained in step b); and d) comparing learning ability assessed in step c) with learning ability assessed using the training protocol of step b) by a control animal to which said pharmaceutical agent has not been administered, wherein the pharmaceutical agent is identified as one having the ability to treat said learning defect in said animal if learning ability assessed in step c) is greater than learning ability by said control animal.

6. The method of claim 5 wherein said animal is a manmmal.

7. The method of claim 5 wherein said animal is a rodent.

8. The method of claim 5 wherein said animal is a Drosophila species.

* * * * *

SEQUENCE LISTING

```
<160> NUMBER OF SEQ ID NOS:   6

<210> SEQ ID NO 1
<211> LENGTH: 2802
<212> TYPE: PRT
<213> ORGANISM: Drosophila

<400> SEQUENCE: 1

Met Thr Gln Lys Pro Gly Glu Trp Ala Ser Ala Leu Leu Ala Arg Phe
1               5                   10                  15

Glu Asp Gln Leu Pro Asn Arg Ile Gly Ala Tyr Gly Thr Gln Ala Arg
            20                  25                  30

Met Ser Gln Asp Gln Leu Val Ala Cys Leu Ile His Ile Ser Arg Tyr
        35                  40                  45

Arg Phe Ser Leu Val Ile Ser Gly Leu Thr Lys Met Leu Gln Arg Val
    50                  55                  60

Asn Glu Ala Ala Leu Gln Asn Arg His Glu Pro Glu Arg Cys Tyr Phe
65                  70                  75                  80

Glu Ser Leu Val Ile Ile Leu Thr Thr Leu Glu Arg Cys Leu Thr Asn
                85                  90                  95

Gln Thr Lys Asp Thr Ala Arg Phe Glu Glu Ala Met Asn Val Lys Leu
            100                 105                 110
```

```
Leu Leu Arg Glu Ile Ser Gln Phe Val Asp Val Gln Ser Asp Ser Asn
        115                 120                 125

Pro Asn Ala Ala Gln Leu Lys Ala Leu Ala Ser Lys Val Leu Phe Ala
130                 135                 140

Leu Ser Gln Asn His Phe Ser Ala Val Phe Asn Arg Ile Ser Ala Arg
145                 150                 155                 160

Ile Gln Glu Leu Thr Ser Cys Ser Glu Glu Asn Pro Asp Tyr Asn Asp
                165                 170                 175

Ile Glu Leu Ile Gln His Ile Asp Met Asp Met Ile Lys Leu Thr Lys
            180                 185                 190

Leu Leu Gln Glu Thr Ile Thr Lys Phe Arg Ser Lys Arg Ala Pro Pro
        195                 200                 205

Leu Ile Leu Leu Tyr Ser Leu Glu Lys Ala Ile Trp Asn Trp Ile Glu
        210                 215                 220

Tyr His Pro Gln Glu Phe Gln Asp Leu Gln Arg Gly Thr Asn Arg Asp
225                 230                 235                 240

Ile Ser Thr Cys Trp Glu Pro Leu Met Asp Phe Val Glu Tyr Phe Lys
                245                 250                 255

Thr Glu Asn Lys Lys Ser Lys Thr Leu Val Trp Pro Leu Gln Met Leu
            260                 265                 270

Leu Leu Ile Leu Asn Pro Ser Cys Leu Glu Ala Val Asn Glu Leu
        275                 280                 285

Gln Gln Ser Glu Lys Glu Lys Glu Lys Asp Lys Glu Lys Val Ala Ser
        290                 295                 300

Lys Ser Ala Gln Ser Thr Ser Arg Asp Lys Asp Phe Ser Ala Lys Gln
305                 310                 315                 320

Phe Ile Glu Ser Ile Lys Arg Gly Leu Gly Gln His Ser Pro Ser Lys
                325                 330                 335

Gln Val Thr Glu Ser Ala Ala Ile Ala Cys Val Lys Leu Cys Lys Ala
            340                 345                 350

Ser Thr Tyr Ile Asn Asn Thr Asp Ser Asn Asn Val Val Phe Lys Leu
        355                 360                 365

Val Gln Phe Phe Ile Asn Asp Leu Lys Ala Leu Leu Phe Asn Pro Ala
        370                 375                 380

Lys Pro Phe Ser Arg Gly Gln Gly Tyr Asn Phe Ala Asp Ile Glu Leu
385                 390                 395                 400

Met Ile Asp Cys Trp Val Ser Cys Phe Arg Ile Asn Pro His Asn Ile
                405                 410                 415

Glu Ala Leu Lys Val Cys Leu Asn Leu Ser Ser Pro Gln Ala Tyr His
            420                 425                 430

Phe Val Ile Val Cys Ser Leu Leu Arg Leu Ala His Ile Tyr Val Asp
        435                 440                 445

Phe Arg Leu Gln Asn Lys Asn Pro Phe Arg Ile Val Asn Gln Pro Arg
        450                 455                 460

Leu Ser Trp Trp Pro Gln Thr Asp Val Val His Tyr Arg Ser Ala Glu
465                 470                 475                 480

Leu Arg Ala Leu Phe Thr Asp Thr Leu Asn Lys Ala Thr Gln Gly Tyr
                485                 490                 495

Ile Ala His Thr Pro Leu Arg Tyr Ile Thr Ser Leu Thr Leu Lys Ser
            500                 505                 510

Lys Asp Thr Gln Lys Gly Leu Thr Arg Ala Glu Glu Gly Pro Ala His
        515                 520                 525
```

```
Lys Met Leu Leu Leu Leu Val Arg Leu Ile His Ala Asp Pro Thr
    530                 535                 540

Leu Leu Leu Asn Thr Gln Gly Lys Val Ala His Glu Val Gln Ser Ser
545                 550                 555                 560

Thr Leu Glu Leu Ile Asn Gly Leu Val Ser Leu Val His Gln Thr Thr
                565                 570                 575

Met Pro Asp Val Ala Gln Glu Ala Met Glu Ala Leu Leu Ala Leu His
            580                 585                 590

Ala Pro Glu Lys Ile Glu Val Trp Asn Pro Glu Ala Pro Ile Asn Thr
        595                 600                 605

Phe Trp Asp Val Ser Ser Gln Val Leu Phe Ser Ile Ser Gln Lys Leu
    610                 615                 620

Ile Gln His Gln Ile Ala Asn Tyr Thr Asp Val Leu Lys Trp Leu Arg
625                 630                 635                 640

Glu Ile Leu Ile Cys Arg Asn Thr Phe Leu Gln Arg His Lys Asp Tyr
                645                 650                 655

Ala His Val Gly Ser Gln Ile Ala Ile Cys Lys Gln Ala His Ile Lys
            660                 665                 670

Met Glu Val Val Phe Phe Met Tyr Leu Trp Ser Val Asp Leu Asp Ala
        675                 680                 685

Val Leu Thr Ser Leu Ser Cys Phe Gly Leu Leu Cys Glu Glu Ala Glu
    690                 695                 700

Ile Cys Cys Ser Ser Asp Glu Leu Thr Val Gly Phe Ile Met Pro Asn
705                 710                 715                 720

Tyr His Ile Tyr Gln Glu Leu Ala Gln Leu Ser Thr Ser Ala Thr Asp
                725                 730                 735

Ser Arg Ile Cys Phe Phe Asp Asn Thr His Gly Asn Val Leu Ser Arg
            740                 745                 750

Leu Thr Leu Gln Lys Arg Ile Met Thr Leu Leu Arg Lys Ile Glu His
        755                 760                 765

Cys Val His Gly Val Gln Pro Ala Trp Glu Glu Thr Phe Arg Asn Trp
    770                 775                 780

Glu Val Ser Ser Lys Val Leu Gln Thr Tyr Pro Lys Cys Lys Gly Glu
785                 790                 795                 800

Asp Gly Gln Ala Glu Val Phe His Arg Gly Met Gly Lys Arg Arg Ala
                805                 810                 815

Ser His Gln Ser Ser Glu His Asp Leu Glu Glu Gln Ile Asn Glu Trp
            820                 825                 830

Ala Asn Met Thr Trp Phe Leu Leu Ala Leu Gly Gly Val Cys Leu His
        835                 840                 845

Lys Arg Ser Ser Ser Arg Gln Met Leu Leu Gln Gln Ser Gln Asn Asn
    850                 855                 860

Ala Ser Leu Gly Ser Leu Ala Gln Asn Ser Leu Tyr Ser Ser Ser Thr
865                 870                 875                 880

Ser Ser Gly His Gly Ser Leu His Pro Ser Thr Val Ser Leu Ser Thr
                885                 890                 895

Leu Pro Pro Ala Pro Pro Gln Asp Val Ser Tyr Cys Pro Val Thr Gln
            900                 905                 910

Phe Val Gly Gln Leu Leu Arg Leu Val Cys Ser Asn Glu Lys Ile
        915                 920                 925

Gly Leu Asn Ile Gln Lys Asn Val Lys Glu Leu Val Gly Glu Glu Met
    930                 935                 940

Ser Thr Gln Leu Tyr Pro Ile Leu Phe Asp Gln Val Arg Ala Ile Val
```

-continued

```
945                 950                 955                 960
Glu Lys Phe Phe Asp Gln Gln Gly Gln Val Asn Val Asn Val Thr Asp
                965                 970                 975
Ile Asn Thr Gln Phe Ile Glu His Thr Ile Tyr Ile Met Lys Ser Ile
                980                 985                 990
Leu Asp Pro Lys Ala Asn Lys Asp Pro Asn Asn Asp Gln Pro Ser Pro
                995                 1000                1005
Ser Glu His Leu Gly Val Thr Ser Ile Glu Gly Met Met Leu Gly Ile
            1010                1015                1020
Val Arg Tyr Val Arg His Leu Asp Met Thr Val Tyr Ala Ile Arg Ile
1025                1030                1035                1040
Lys Thr Lys Leu Cys Gln Leu Val Glu Val Met Met Lys Arg Arg Asp
                1045                1050                1055
Asp Leu Ala Phe Arg Gln Glu Met Lys Phe Arg Asn Lys Leu Val Glu
                1060                1065                1070
Tyr Leu Thr Asp Trp Val Met Gly Thr Ser His Gln Ile Ala Pro Pro
                1075                1080                1085
Ser Ser Ala Asp Ala Ala Ile Leu Thr Asn Thr Ser Leu Ile Phe Arg
            1090                1095                1100
Asp Leu Asp Gln Ala Cys Met Glu Ala Val Ala Ala Leu Leu Arg Gly
1105                1110                1115                1120
Leu Pro Leu Gln Pro Glu Glu Ser Asp Arg Gly Asp Leu Met Asp Ala
                1125                1130                1135
Lys Ser Ala Leu Phe Leu Lys Tyr Phe Thr Leu Phe Met Asn Leu Leu
                1140                1145                1150
Asn Asp Cys Ile Asp Ser Ser Glu Ala Glu Lys Glu Met Asn Asn Thr
                1155                1160                1165
Pro Leu Leu Pro Pro Arg Pro Pro Met Ala Ala Gly Lys Leu Thr Ala
            1170                1175                1180
Leu Arg Asn Ala Thr Ile Leu Ala Met Ser Asn Leu Leu Gly Ala Asn
1185                1190                1195                1200
Ile Asp Ser Gly Leu Met His Ser Ile Asp Leu Gly Tyr Asn Pro Asp
                1205                1210                1215
Leu Gln Thr Arg Ala Ala Phe Met Glu Val Leu Thr Gln Ile Leu Gln
            1220                1225                1230
Gln Gly Thr Glu Phe Asp Thr Leu Ala Glu Thr Val Leu Ala Asp Arg
            1235                1240                1245
Phe Glu Gln Leu Val Gln Leu Val Thr Met Ile Ser Asp Lys Gly Glu
            1250                1255                1260
Leu Pro Ile Ala Met Ala Leu Ala Asn Val Val Thr Thr Ser Gln Met
1265                1270                1275                1280
Asp Glu Leu Ala Arg Val Leu Val Thr Leu Phe Asp Ala Lys His Leu
                1285                1290                1295
Leu Ser Pro Leu Leu Trp Asn Met Phe Tyr Arg Glu Val Glu Val Ser
            1300                1305                1310
Asp Cys Met Gln Thr Leu Phe Arg Gly Asn Ser Leu Gly Ser Lys Ile
            1315                1320                1325
Met Ala Phe Cys Phe Lys Ile Tyr Gly Ala Ser Tyr Leu Gln Met Leu
            1330                1335                1340
Leu Glu Pro Leu Ile Arg Pro Leu Leu Asp Glu Glu Glu Thr Cys
1345                1350                1355                1360
Phe Glu Val Asp Pro Ala Arg Leu Asp Pro Thr Glu Asp Ile Glu Gln
                1365                1370                1375
```

-continued

```
His Arg Asn Asn Leu Ile Ala Leu Thr Gln Lys Val Phe Asp Ala Ile
            1380                1385                1390

Ile Asn Ser Ser Asp Arg Phe Pro Pro Gln Leu Arg Ser Met Cys His
    1395                1400                1405

Cys Leu Tyr Gln Val Leu Ser Lys Arg Phe Pro Asn Leu Leu Gln Asn
    1410                1415                1420

Asn Ile Gly Ala Val Gly Thr Val Ile Phe Leu Arg Phe Ile Asn Pro
1425                1430                1435                1440

Ala Ile Val Ser Pro Gln Glu Leu Gly Ile Val Asp Lys Gln Val His
                1445                1450                1455

Ser Ser Ala Lys Arg Gly Leu Met Leu Met Ser Lys Ile Leu Gln Asn
                1460                1465                1470

Ile Ala Asn His Val Glu Phe Ser Lys Glu Gln His Met Leu Cys Phe
                1475                1480                1485

Asn Asp Phe Leu Arg Asp His Phe Glu Ala Gly Arg Arg Phe Phe Ile
                1490                1495                1500

Gln Ile Ala Ser Asp Cys Glu Thr Val Asp Gln Thr Ser His Ser Met
1505                1510                1515                1520

Ser Phe Ile Ser Asp Ala Asn Val Leu Ala Leu His Arg Leu Leu Trp
                1525                1530                1535

Thr His Gln Glu Lys Ile Gly Asp Tyr Leu Ser Ser Ser Arg Asp His
                1540                1545                1550

Lys Ala Val Gly Arg Arg Pro Phe Asp Lys Met Ala Thr Leu Leu Ala
                1555                1560                1565

Tyr Leu Gly Pro Pro Glu His Lys Pro Val Asp Ser His Met Met Phe
    1570                1575                1580

Ser Ser Tyr Ala Arg Trp Ser Ser Ile Asp Met Ser Ser Thr Asn Phe
1585                1590                1595                1600

Glu Glu Ile Met Val Lys His Gln Met His Glu Lys Glu Glu Phe Lys
                1605                1610                1615

Thr Leu Lys Ser Met Asn Ile Phe Tyr Gln Ala Gly Thr Ser Lys Ser
                1620                1625                1630

Gly Tyr Pro Val Phe Tyr Tyr Ile Ala Arg Arg Tyr Lys Ile Gly Glu
                1635                1640                1645

Thr Asn Gly Asp Leu Leu Ile Tyr His Val Ile Leu Thr Leu Lys Pro
1650                1655                1660

Phe Cys His Ser Pro Phe Glu Val Val Ile Asp Phe Thr His Thr Cys
1665                1670                1675                1680

Ser Asp Asn Arg Phe Arg Thr Glu Phe Leu Gln Lys Trp Phe Tyr Val
                1685                1690                1695

Leu Pro Thr Val Ala Tyr Glu Asn Val His Ala Val Tyr Ile Tyr Asn
                1700                1705                1710

Cys Asn Ser Trp Val Arg Glu Tyr Thr Lys Phe His Asp Arg Ile Leu
                1715                1720                1725

Ala Pro Leu Lys Gly Asn Arg Lys Leu Leu Phe Leu Glu Ser Pro Asn
                1730                1735                1740

Lys Leu Thr Asp Phe Ile Asp Ala Glu Gln Gln Lys Leu Pro Gly Ala
1745                1750                1755                1760

Thr Leu Ser Leu Asp Glu Asp Leu Lys Val Phe Ser Asn Ala Leu Lys
                1765                1770                1775

Leu Ser His Lys Asp Thr Lys Val Ala Ile Lys Val Gly Pro Thr Ala
                1780                1785                1790
```

-continued

```
Leu Gln Ile Thr Ser Ala Glu Lys Thr Lys Val Leu Ala His Ser Val
        1795                1800                1805
Leu Leu Asn Asp Val Tyr Tyr Ala Ser Glu Ile Glu Glu Val Cys Leu
    1810                1815                1820
Val Asp Asp Asn Gln Phe Thr Leu Ser Ile Thr Asn Glu Ser Gly Gln
1825                1830                1835                1840
Leu Ser Phe Ile His Asn Asp Cys Asp Asn Ile Val Gln Ala Ile Ile
            1845                1850                1855
His Ile Arg Asn Arg Trp Glu Leu Ser Gln Pro Asp Ser Val Thr Val
        1860                1865                1870
Gln Lys Ile Arg Pro Lys Asp Val Pro Gly Thr Leu Leu Asn Met
    1875                1880                1885
Ala Leu Leu Asn Leu Gly Ser Cys Asp Pro Asn Leu Arg Thr Ala Ala
    1890                1895                1900
Tyr Asn Leu Leu Cys Ala Leu Thr Ala Thr Phe Asp Leu Lys Ile Glu
1905                1910                1915                1920
Gly Gln Leu Leu Glu Thr Gln Gly Leu Cys Ile Pro Ser Asn Asn Thr
            1925                1930                1935
Ile Phe Ile Lys Ser Val Ser Glu Lys Leu Ala Thr Asn Glu Pro His
            1940                1945                1950
Leu Thr Leu Glu Phe Leu Glu Glu Ser Ile Gln Gly Phe Gln Arg Thr
        1955                1960                1965
Thr Ile Glu Leu Lys His Leu Cys Leu Glu Tyr Met Thr Pro Trp Leu
    1970                1975                1980
Lys Asn Leu Val Lys Phe Cys Lys Ser Asn Asp Asp Ser Lys Lys Leu
1985                1990                1995                2000
Lys Val Ser Gln Ile Leu Asp Lys Leu Ile Asn Leu Thr Ile Asp Gln
            2005                2010                2015
Lys Glu Met Tyr Pro Ser Val Gln Ala Lys Ile Trp Gly Ser Ile Gly
        2020                2025                2030
Gln Ile Pro Glu Leu Ile Asp Met Val Leu Asp Asn Phe Leu His Lys
        2035                2040                2045
Ser Ile Thr Tyr Gly Leu Gly Ser Pro Gln Val Glu Ile Met Ala Asp
2050                2055                2060
Thr Ala Val Ala Leu Ala Ser Ala Asn Val Gln Leu Val Ser Lys Lys
2065                2070                2075                2080
Val Ile Thr Arg Ile Cys Arg Val Met Asp Lys Ser Cys Thr Asn Pro
            2085                2090                2095
Thr Gln Tyr Leu Glu Gln His Met Met Trp Asp Asp Ile Ala Ile Leu
        2100                2105                2110
Gly Arg Tyr Leu Leu Met Leu Ser Phe Asn Asn Cys Leu Asp Val Ala
        2115                2120                2125
Thr Ser Val Pro Tyr Leu Phe His Thr Ile Thr Phe Leu Val Cys Ser
        2130                2135                2140
Gly Ser Leu Ser Met Arg Ala Ser Thr His Gly Leu Val Ile Asn Ile
2145                2150                2155                2160
Ile His Ser Leu Cys Thr Cys Thr Asn Pro Ser Phe Ser Glu Glu Ala
            2165                2170                2175
Gln Arg Val Leu Arg Leu Ser Leu Asp Glu Phe Ser Leu Pro Lys Phe
        2180                2185                2190
Tyr Leu Leu Phe Gly Ile Ser Lys Val Lys Ser Ala Ala Val Thr Ala
        2195                2200                2205
Phe Arg Ser Ser Cys Arg His Pro Thr Asp Lys Trp Leu Gly Asn Glu
```

-continued

```
           2210                2215                2220
Arg Val Thr Gln Pro Leu Pro Ala Asp Arg Glu Arg Leu Ser Leu Pro
2225                2230                2235                2240

Ser Leu Glu Val Ile Thr Asp Ala Leu Leu Glu Ile Met Glu Ala Cys
                2245                2250                2255

Met Arg Asp Val Pro Asp Cys Glu Trp Leu Asn Thr Trp Thr Ser Leu
                2260                2265                2270

Ala Arg Ser Phe Ala Phe Cys Tyr Asn Pro Ala Leu Gln Pro Arg Ala
            2275                2280                2285

Leu Ile Val Tyr Gly Cys Ile Ser Lys Ser Val Thr Asp His Glu Val
        2290                2295                2300

Lys Gln Leu Leu Arg Ile Leu Val Lys Ala Leu Glu Ser Phe Asn Asp
2305                2310                2315                2320

Leu Ile Leu Ile Glu Ala Leu Val Met Cys Leu Thr Arg Ile Gln Pro
                2325                2330                2335

Leu Leu Arg Pro Glu Ser Pro Ile His Arg Ala Leu Phe Trp Val Ala
                2340                2345                2350

Ile Ser Val Leu Gln Leu Asp Glu Ile Thr Leu Tyr Gly Ala Gly Leu
        2355                2360                2365

Ala Leu Leu Glu Gln Asn Leu His Thr Leu Lys Ser Gln Gly Cys Phe
    2370                2375                2380

Asp Lys Lys Glu Thr Ile Ala Glu Val Met Met Lys Thr Arg Glu Lys
2385                2390                2395                2400

Leu Glu Trp His Phe Lys Gln Leu Asp His Ala Val Gly Leu Ser Phe
                2405                2410                2415

Arg Ser Asn Phe His Phe Ala Leu Val Gly His Leu Ile Lys Gly Phe
                2420                2425                2430

Arg His Pro Thr Pro Thr Thr Val Ser Arg Thr Ser Arg Val Leu Thr
            2435                2440                2445

Met Leu Leu Gly Ile Tyr Ala Lys Pro Leu His Arg Asp Lys Phe Glu
        2450                2455                2460

Val Thr Pro Asp Ser Val Ala Tyr Leu Thr Ala Leu Val Ala Val Ser
2465                2470                2475                2480

Glu Glu Val Arg Ser Arg Cys His Val Lys His Ala Leu Pro Arg Trp
                2485                2490                2495

Pro Ala Asp Leu Ser Ser Ser Val Glu Asn Gly Glu Ala Ser Gly Gly
            2500                2505                2510

Val Gln Ala Ile Gly Leu Pro Leu Ser Arg Arg Gln Lys Ser Trp Asp
        2515                2520                2525

Ile Leu Asp Gln Ser Ala Leu Gln Phe Ala Arg Gln His Lys Val Pro
    2530                2535                2540

Thr Leu Gln Asn Ala Arg Val Leu Phe Lys Thr Gln Arg Ser Phe Ser
2545                2550                2555                2560

Val Pro Thr Thr Lys Asp Pro Asn Asn Ala Thr Gly Ile Glu Glu Arg
                2565                2570                2575

Gln Glu Arg Gly Ser Arg Ser Ser Val Ser Asn Glu Ser Asn Val Leu
            2580                2585                2590

Leu Asp Pro Glu Val Leu Pro Asp Leu Ser Ile Gln Ala Leu Val Leu
        2595                2600                2605

Thr Val Leu Ala Thr Leu Val Lys Tyr Ser Ser Asp Glu Gly Glu Thr
    2610                2615                2620

Arg Val Leu Tyr Gln Tyr Leu Ala Glu Gly Ser Val Val Phe Pro Lys
2625                2630                2635                2640
```

-continued

```
Val Phe Pro Val Ile His Ser Leu Leu Asp Gln Lys Ile Asn Asn Ile
            2645                2650                2655

Leu Ser Val Ser His Asp Gln Val Val Leu Asn Ser Val Gln Asn Ile
            2660                2665                2670

Ile Gln Asn Met Leu Ala Ser Glu Asp Pro Ser Gln Gln Leu His
            2675                2680                2685

Phe Leu Gln Ser Cys Gly Phe Gly Gly Leu Trp Arg Phe Ala Gly Pro
            2690                2695                2700

Phe Thr Lys Tyr Asn Met Met Gly Glu Ser Ser Glu Leu Phe Val Asn
2705                2710                2715                2720

Cys Leu Glu Ala Met Val Glu Thr Cys Leu Pro Gly Asp Glu Ser Ala
            2725                2730                2735

Pro Val Pro Pro Ser Pro Arg Pro Tyr Asn Leu Ser Ser Ser Leu Ser
            2740                2745                2750

Ser Leu Thr Leu Gly Ser Pro Thr Asp Lys Ala Phe Ser Ser Glu Ser
            2755                2760                2765

Leu Asp Phe Tyr Asp Asn Cys Pro Gly Ser Val Ser Ser Leu Arg Arg
            2770                2775                2780

Ala Ser His Ser Lys Ser Arg Ala Lys His Arg Ile Asn Asp Ser Pro
2785                2790                2795                2800

Ser His
```

```
<210> SEQ ID NO 2
<211> LENGTH: 2818
<212> TYPE: PRT
<213> ORGANISM: Human

<400> SEQUENCE: 2

Met Ala Ala His Arg Pro Val Glu Trp Val Gln Ala Val Val Ser Arg
1               5                   10                  15

Phe Asp Glu Gln Leu Pro Ile Lys Thr Gly Gln Gln Asn Thr His Thr
            20                  25                  30

Lys Val Ser Thr Glu His Asn Lys Glu Cys Leu Ile Asn Ile Ser Lys
        35                  40                  45

Tyr Lys Phe Ser Leu Val Ile Ser Gly Leu Thr Thr Ile Leu Lys Asn
    50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
            115                 120                 125

Gln His Ala Ala Glu Leu Arg Asn Ser Ala Ser Gly Val Leu Phe Ser
        130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                165                 170                 175

Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
        195                 200                 205
```

```
Gln Leu Ala Val Ile Asn Ser Leu Glu Lys Ala Phe Trp Asn Trp Val
    210                 215                 220
Glu Asn Tyr Pro Asp Glu Phe Thr Lys Leu Tyr Gln Ile Pro Gln Thr
225                 230                 235                 240
Asp Met Ala Glu Cys Ala Glu Lys Leu Phe Asp Leu Val Asp Gly Phe
                245                 250                 255
Ala Glu Ser Thr Lys Arg Lys Ala Ala Val Trp Pro Leu Gln Ile Ile
            260                 265                 270
Leu Leu Ile Leu Cys Pro Glu Ile Ile Gln Asp Ile Ser Lys Asp Val
        275                 280                 285
Val Asp Glu Asn Asn Met Asn Lys Lys Leu Phe Leu Asp Ser Leu Arg
    290                 295                 300
Lys Ala Leu Ala Gly His Gly Gly Ser Arg Gln Leu Thr Glu Ser Ala
305                 310                 315                 320
Ala Ile Ala Cys Val Lys Leu Cys Lys Ala Ser Thr Tyr Ile Asn Trp
                325                 330                 335
Glu Asp Asn Ser Val Ile Phe Leu Leu Val Gln Ser Met Val Val Asp
            340                 345                 350
Leu Lys Asn Leu Leu Phe Asn Pro Ser Lys Pro Phe Ser Arg Gly Ser
        355                 360                 365
Gln Pro Ala Asp Val Asp Leu Met Ile Asp Cys Leu Val Ser Cys Phe
    370                 375                 380
Arg Ile Ser Pro His Asn Asn Gln His Phe Lys Ile Cys Leu Ala Gln
385                 390                 395                 400
Asn Ser Pro Ser Thr Phe His Tyr Val Leu Val Asn Ser Leu His Arg
                405                 410                 415
Ile Ile Thr Asn Ser Ala Leu Asp Trp Trp Pro Lys Ile Asp Ala Val
            420                 425                 430
Tyr Cys His Ser Val Glu Leu Arg Asn Met Phe Gly Glu Thr Leu His
        435                 440                 445
Lys Ala Val Gln Gly Cys Gly Ala His Pro Ala Ile Arg Met Ala Pro
    450                 455                 460
Ser Leu Thr Phe Lys Glu Lys Val Thr Ser Leu Lys Phe Lys Glu Lys
465                 470                 475                 480
Pro Thr Asp Leu Glu Thr Arg Ser Tyr Lys Tyr Leu Leu Leu Ser Met
                485                 490                 495
Val Lys Leu Ile His Ala Asp Pro Lys Leu Leu Leu Cys Asn Pro Arg
            500                 505                 510
Lys Gln Gly Pro Glu Thr Gln Gly Ser Thr Ala Glu Leu Ile Thr Gly
        515                 520                 525
Leu Val Gln Leu Val Pro Gln Ser His Met Pro Glu Ile Ala Gln Glu
    530                 535                 540
Ala Met Glu Ala Leu Leu Val Leu His Gln Leu Asp Ser Ile Asp Leu
545                 550                 555                 560
Trp Asn Pro Asp Ala Pro Val Glu Thr Phe Trp Glu Ile Ser Ser Gln
                565                 570                 575
Met Leu Phe Tyr Ile Cys Lys Lys Leu Thr Ser His Gln Met Leu Ser
            580                 585                 590
Ser Thr Glu Ile Leu Lys Trp Leu Arg Glu Ile Leu Ile Cys Arg Asn
        595                 600                 605
Lys Phe Leu Leu Lys Asn Lys Gln Ala Asp Arg Ser Ser Cys His Phe
    610                 615                 620
```

```
Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
            645                 650                 655

Ser Leu Arg Lys Gly Lys Gly Asn Ser Ser Met Asp Ser Ala Ala Cys
            660                 665                 670

Cys Ser Gly Thr Pro Pro Ile Cys Arg Gln Ala Gln Thr Lys Leu Glu
            675                 680                 685

Val Ala Leu Tyr Met Phe Leu Trp Asn Pro Asp Thr Glu Ala Val Leu
690                 695                 700

Val Ala Met Ser Cys Phe Arg His Leu Cys Glu Glu Ala Asp Ile Arg
705                 710                 715                 720

Cys Gly Val Asp Glu Val Ser Val His Asn Leu Leu Pro Asn Tyr Asn
                725                 730                 735

Thr Phe Met Glu Phe Ala Ser Val Ser Asn Met Met Ser Thr Gly Arg
                740                 745                 750

Ala Ala Leu Gln Lys Arg Val Met Ala Leu Leu Arg Arg Ile Glu His
            755                 760                 765

Pro Thr Ala Gly Asn Thr Glu Ala Trp Glu Asp Thr His Ala Lys Trp
770                 775                 780

Glu Gln Ala Thr Lys Leu Ile Leu Asn Tyr Pro Lys Ala Lys Met Glu
785                 790                 795                 800

Asp Gly Gln Ala Ala Glu Ser Leu His Lys Thr Ile Val Lys Arg Arg
                805                 810                 815

Met Ser His Val Ser Gly Gly Ser Ile Asp Leu Ser Asp Thr Asp
                820                 825                 830

Ser Leu Gln Glu Trp Ile Asn Met Thr Gly Phe Leu Cys Ala Leu Gly
            835                 840                 845

Gly Val Cys Leu Gln Gln Arg Ser Asn Ser Gly Leu Ala Thr Tyr Ser
    850                 855                 860

Pro Pro Met Gly Pro Val Ser Glu Arg Lys Gly Ser Met Ile Ser Val
865                 870                 875                 880

Met Ser Ser Glu Gly Asn Ala Asp Thr Pro Val Ser Lys Phe Met Asp
                885                 890                 895

Arg Leu Leu Ser Leu Met Val Cys Asn His Glu Lys Val Gly Leu Gln
                900                 905                 910

Ile Arg Thr Asn Val Lys Asp Leu Val Gly Leu Glu Leu Ser Pro Ala
            915                 920                 925

Leu Tyr Pro Met Leu Phe Asn Lys Leu Lys Asn Thr Ile Ser Lys Phe
930                 935                 940

Phe Asp Ser Gln Gly Gln Val Leu Leu Thr Asp Thr Asn Thr Gln Phe
945                 950                 955                 960

Val Glu Gln Thr Ile Ala Ile Met Lys Asn Leu Leu Asp Asn His Thr
                965                 970                 975

Glu Gly Ser Ser Glu His Leu Gly Gln Ala Ser Ile Glu Thr Met Met
                980                 985                 990

Leu Asn Leu Val Arg Tyr Val Arg Val Leu Gly Asn Met Val His Ala
            995                 1000                1005

Ile Gln Ile Lys Thr Lys Leu Cys Gln Leu Val Glu Val Met Met Ala
        1010                1015                1020

Arg Arg Asp Asp Leu Ser Phe Cys Gln Glu Met Lys Phe Arg Asn Lys
1025                1030                1035                1040

Met Val Glu Tyr Leu Thr Asp Trp Val Met Gly Thr Ser Asn Gln Ala
```

-continued

```
                1045                1050                1055
Ala Asp Asp Val Lys Cys Leu Thr Arg Asp Leu Asp Gln Ala Ser
            1060                1065                1070
Met Glu Ala Val Val Ser Leu Leu Ala Gly Leu Pro Leu Gln Pro Glu
        1075                1080                1085
Glu Gly Asp Gly Val Glu Leu Met Glu Ala Lys Ser Gln Leu Phe Leu
        1090                1095                1100
Lys Tyr Phe Thr Leu Phe Met Asn Leu Leu Asn Asp Cys Ser Glu Val
1105                1110                1115                1120
Glu Asp Glu Ser Ala Gln Thr Gly Gly Arg Lys Arg Gly Met Ser Arg
                1125                1130                1135
Arg Leu Ala Ser Leu Arg His Cys Thr Val Leu Ala Met Ser Asn Leu
            1140                1145                1150
Leu Asn Ala Asn Val Asp Ser Gly Leu Met His Ser Ile Gly Leu Gly
            1155                1160                1165
Tyr His Lys Asp Leu Gln Thr Arg Ala Thr Phe Met Glu Val Leu Thr
        1170                1175                1180
Lys Ile Leu Gln Gln Gly Thr Glu Phe Asp Thr Leu Ala Glu Thr Val
1185                1190                1195                1200
Leu Ala Asp Arg Phe Glu Arg Leu Val Glu Leu Val Ile Met Met Gly
            1205                1210                1215
Asp Gln Gly Glu Leu Pro Ile Ala Met Ala Leu Ala Asn Val Val Pro
            1220                1225                1230
Cys Ser Gln Trp Asp Glu Leu Ala Arg Val Leu Val Thr Leu Phe Asp
        1235                1240                1245
Ser Arg His Leu Leu Tyr Gln Leu Leu Trp Asn Met Phe Ser Lys Glu
        1250                1255                1260
Val Glu Leu Ala Asp Ser Met Gln Thr Leu Phe Arg Gly Asn Ser Leu
1265                1270                1275                1280
Ala Ser Lys Ile Met Thr Phe Cys Phe Lys Val Tyr Gly Ala Thr Tyr
            1285                1290                1295
Leu Gln Lys Leu Leu Asp Pro Leu Leu Arg Ile Val Ile Thr Ser Ser
        1300                1305                1310
Asp Trp Gln His Val Ser Phe Glu Val Asp Pro Thr Arg Leu Glu Pro
        1315                1320                1325
Ser Glu Ser Leu Glu Glu Asn Gln Arg Asn Leu Leu Gln His Thr Glu
        1330                1335                1340
Lys Phe Phe His Ala Ile Ile Ser Ser Ser Ser Glu Phe Pro Pro Gln
1345                1350                1355                1360
Leu Arg Ser Val Cys His Cys Leu Tyr Gln Val Val Ser Gln Arg Phe
            1365                1370                1375
Pro Gln Asn Ser Ile Gly Ala Val Gly Ser Ala Met Phe Leu Arg Phe
            1380                1385                1390
Ile Asn Pro Ala Ile Val Ser Pro Tyr Glu Ala Gly Ile Leu Asp Lys
        1395                1400                1405
Lys Pro Pro Arg Ile Glu Arg Gly Leu Lys Leu Met Ser Lys Ile
        1410                1415                1420
Leu Gln Ser Ile Ala Asn His Val Leu Phe Thr Lys Glu Glu His Met
1425                1430                1435                1440
Arg Pro Phe Asn Asp Phe Val Lys Ser Asn Phe Asp Ala Ala Arg Arg
                1445                1450                1455
Phe Phe Leu Asp Ile Ala Ser Asp Cys Pro Thr Ser Asp Ala Val Asn
            1460                1465                1470
```

```
His Ser Leu Ser Phe Ile Ser Asp Gly Asn Val Leu Ala Leu His Arg
        1475                1480                1485
Leu Leu Trp Asn Asn Gln Glu Lys Ile Gly Gln Tyr Leu Ser Ser Asn
        1490                1495                1500
Arg Asp His Lys Ala Val Gly Arg Arg Pro Phe Asp Lys Met Ala Thr
1505                1510                1515                1520
Leu Leu Ala Tyr Leu Gly Pro Pro Glu His Lys Pro Val Ala Asp Thr
                1525                1530                1535
His Trp Ser Ser Leu Asn Leu Thr Ser Ser Lys Phe Glu Glu Phe Met
        1540                1545                1550
Thr Arg His Gln Val His Glu Lys Glu Glu Phe Lys Ala Leu Lys Thr
        1555                1560                1565
Leu Ser Ile Phe Tyr Gln Ala Gly Thr Ser Lys Ala Gly Asn Pro Ile
        1570                1575                1580
Phe Tyr Tyr Val Ala Arg Arg Phe Lys Thr Gly Gln Ile Asn Gly Asp
1585                1590                1595                1600
Leu Leu Ile Tyr His Val Leu Leu Thr Leu Lys Pro Tyr Tyr Ala Lys
                1605                1610                1615
Pro Tyr Glu Ile Val Val Asp Leu Thr His Thr Gly Pro Ser Asn Arg
        1620                1625                1630
Phe Lys Thr Asp Phe Leu Ser Lys Trp Phe Val Val Phe Pro Gly Phe
        1635                1640                1645
Ala Tyr Asp Asn Val Ser Ala Val Tyr Ile Tyr Asn Cys Asn Ser Trp
        1650                1655                1660
Val Arg Glu Tyr Thr Lys Tyr His Glu Arg Leu Leu Thr Gly Leu Lys
1665                1670                1675                1680
Gly Ser Lys Arg Leu Val Phe Ile Asp Cys Pro Gly Lys Leu Ala Glu
                1685                1690                1695
His Ile Glu His Glu Gln Gln Lys Leu Pro Ala Ala Thr Leu Ala Leu
        1700                1705                1710
Glu Glu Asp Leu Lys Val Phe His Asn Ala Leu Lys Leu Ala His Lys
        1715                1720                1725
Asp Thr Lys Val Ser Ile Lys Val Gly Ser Thr Ala Val Gln Val Thr
        1730                1735                1740
Ser Ala Glu Arg Thr Lys Val Leu Gly Gln Ser Val Phe Leu Asn Asp
1745                1750                1755                1760
Ile Tyr Tyr Ala Ser Glu Ile Glu Glu Ile Cys Leu Val Asp Glu Asn
                1765                1770                1775
Gln Phe Thr Leu Thr Ile Ala Asn Gln Gly Thr Pro Leu Thr Phe Met
        1780                1785                1790
His Gln Glu Cys Glu Ala Ile Val Gln Ser Ile Ile His Ile Arg Thr
        1795                1800                1805
Arg Trp Glu Leu Ser Gln Pro Asp Ser Ile Pro Gln His Thr Lys Ile
        1810                1815                1820
Arg Pro Lys Asp Val Pro Gly Thr Leu Leu Asn Ile Ala Leu Leu Asn
1825                1830                1835                1840
Leu Gly Ser Ser Asp Pro Ser Leu Arg Ser Ala Ala Tyr Asn Leu Leu
                1845                1850                1855
Cys Ala Leu Thr Cys Thr Phe Asn Leu Lys Ile Glu Gly Gln Leu Leu
        1860                1865                1870
Glu Thr Ser Gly Leu Cys Ile Pro Ala Asn Asn Thr Leu Phe Ile Val
        1875                1880                1885
```

```
Ser Ile Ser Lys Thr Leu Ala Ala Asn Glu Pro His Leu Thr Leu Glu
    1890                1895                1900

Phe Leu Glu Glu Cys Ile Ser Gly Phe Ser Lys Ser Ile Glu Leu
1905            1910                1915                1920

Lys His Leu Cys Leu Glu Tyr Met Thr Pro Trp Leu Ser Asn Leu Val
                1925                1930                1935

Arg Phe Cys Lys His Asn Asp Asp Ala Lys Arg Gln Arg Val Thr Ala
            1940                1945                1950

Ile Leu Asp Lys Leu Ile Thr Met Thr Ile Asn Glu Lys Gln Met Tyr
                1955                1960                1965

Pro Ser Ile Gln Ala Lys Ile Trp Gly Ser Leu Gly Gln Ile Thr Asp
            1970                1975                1980

Leu Leu Asp Val Val Leu Asp Ser Phe Ile Lys Thr Ser Ala Thr Gly
1985                1990                1995                2000

Gly Leu Gly Ser Ile Lys Ala Glu Val Met Ala Asp Thr Ala Val Ala
                2005                2010                2015

Leu Ala Ser Gly Asn Val Lys Leu Val Ser Ser Lys Val Ile Gly Arg
            2020                2025                2030

Met Cys Lys Ile Ile Asp Lys Thr Cys Leu Ser Pro Thr Pro Thr Leu
            2035                2040                2045

Glu Gln His Leu Met Trp Asp Asp Ile Ala Ile Leu Ala Arg Tyr Met
            2050                2055                2060

Leu Met Leu Ser Phe Asn Asn Ser Leu Asp Val Ala Ala His Leu Pro
2065                2070                2075                2080

Tyr Leu Phe His Val Val Thr Phe Leu Val Ala Thr Gly Pro Leu Ser
                2085                2090                2095

Leu Arg Ala Ser Thr His Gly Leu Val Ile Asn Ile Ile His Ser Leu
            2100                2105                2110

Cys Thr Cys Ser Gln Leu His Phe Ser Glu Glu Thr Lys Gln Val Leu
            2115                2120                2125

Arg Leu Ser Leu Thr Glu Phe Ser Leu Pro Lys Phe Tyr Leu Leu Phe
            2130                2135                2140

Gly Ile Ser Lys Val Lys Ser Ala Ala Val Ile Ala Phe Arg Ser Ser
2145                2150                2155                2160

Tyr Arg Asp Arg Ser Phe Ser Pro Gly Ser Tyr Glu Arg Glu Thr Phe
                2165                2170                2175

Ala Leu Thr Ser Leu Glu Thr Val Thr Glu Ala Leu Leu Glu Ile Met
            2180                2185                2190

Glu Ala Cys Met Arg Asp Ile Pro Thr Cys Lys Trp Leu Asp Gln Trp
            2195                2200                2205

Thr Glu Leu Ala Gln Arg Phe Ala Phe Gln Tyr Asn Pro Ser Leu Gln
            2210                2215                2220

Pro Arg Ala Leu Val Val Phe Gly Cys Ile Ser Lys Arg Val Ser His
2225                2230                2235                2240

Gly Gln Ile Lys Gln Ile Ile Arg Ile Leu Ser Lys Ala Leu Glu Ser
                2245                2250                2255

Cys Leu Lys Gly Pro Asp Thr Tyr Asn Ser Gln Val Leu Ile Glu Ala
            2260                2265                2270

Thr Val Ile Ala Leu Thr Lys Leu Gln Pro Leu Leu Asn Lys Asp Ser
            2275                2280                2285

Pro Leu His Lys Ala Leu Phe Trp Val Ala Val Ala Val Leu Gln Leu
            2290                2295                2300

Asp Glu Val Asn Leu Tyr Ser Ala Gly Thr Ala Leu Leu Glu Gln Asn
```

-continued

```
          2305                2310                2315                2320
Leu His Thr Leu Asp Ser Leu Arg Ile Phe Asn Asp Lys Ser Pro Glu
              2325                2330                2335
Glu Val Phe Met Ala Ile Arg Asn Pro Leu Trp His Cys Lys Gln
              2340                2345                2350
Met Asp His Phe Val Gly Leu Asn Phe Asn Ser Asn Phe Asn Phe Ala
              2355                2360                2365
Leu Val Gly His Leu Leu Lys Gly Tyr Arg His Pro Ser Pro Ala Ile
              2370                2375                2380
Val Ala Arg Thr Val Arg Ile Leu His Thr Leu Thr Leu Val Asn
2385                2390                2395                2400
Lys His Arg Asn Cys Asp Lys Phe Glu Val Asn Thr Gln Ser Val Ala
              2405                2410                2415
Tyr Leu Ala Ala Leu Leu Thr Val Ser Glu Glu Val Arg Ser Arg Cys
              2420                2425                2430
Ser Leu Lys His Arg Lys Ser Leu Leu Leu Thr Asp Ile Ser Met Glu
              2435                2440                2445
Asn Val Pro Met Asp Thr Tyr Pro Ile His His Gly Asp Pro Ser Tyr
              2450                2455                2460
Arg Thr Leu Lys Glu Thr Gln Pro Trp Ser Pro Lys Gly Ser Glu
2465                2470                2475                2480
Gly Tyr Leu Ala Ala Thr Tyr Pro Thr Val Gly Gln Thr Ser Pro Arg
              2485                2490                2495
Ala Arg Lys Ser Met Ser Leu Asp Met Gly Gln Pro Ser Gln Ala Asn
              2500                2505                2510
Thr Lys Lys Leu Leu Gly Thr Arg Lys Ser Phe Asp His Leu Ile Ser
              2515                2520                2525
Asp Thr Lys Ala Pro Lys Arg Gln Glu Met Glu Ser Gly Ile Thr Thr
              2530                2535                2540
Pro Pro Lys Met Arg Arg Val Ala Glu Thr Asp Tyr Glu Met Glu Thr
2545                2550                2555                2560
Gln Arg Ile Ser Ser Ser Gln Gln His Pro His Leu Arg Lys Val Ser
              2565                2570                2575
Val Ser Glu Ser Asn Val Leu Leu Asp Glu Glu Val Leu Thr Asp Pro
              2580                2585                2590
Lys Ile Gln Ala Leu Leu Leu Thr Val Leu Ala Thr Leu Val Lys Tyr
              2595                2600                2605
Thr Thr Asp Glu Phe Asp Gln Arg Ile Leu Tyr Glu Tyr Leu Ala Glu
              2610                2615                2620
Ala Ser Val Val Phe Pro Lys Val Phe Pro Val Val His Asn Leu Leu
2625                2630                2635                2640
Asp Ser Lys Ile Asn Thr Leu Leu Ser Leu Cys Gln Asp Pro Asn Leu
              2645                2650                2655
Leu Asn Pro Ile His Gly Ile Val Gln Ser Val Val Tyr His Glu Glu
              2660                2665                2670
Ser Pro Pro Gln Tyr Gln Thr Ser Tyr Leu Gln Ser Phe Gly Phe Asn
              2675                2680                2685
Gly Leu Trp Arg Phe Ala Gly Pro Phe Ser Lys Gln Thr Gln Ile Pro
              2690                2695                2700
Asp Tyr Ala Glu Leu Ile Val Lys Phe Leu Asp Ala Leu Ile Asp Thr
2705                2710                2715                2720
Tyr Leu Pro Gly Ile Asp Glu Glu Thr Ser Glu Glu Ser Leu Leu Thr
              2725                2730                2735
```

-continued

```
Pro Thr Ser Pro Tyr Pro Pro Ala Leu Gln Ser Gln Leu Ser Ile Thr
            2740            2745                2750

Ala Asn Leu Asn Leu Ser Asn Ser Met Thr Ser Leu Ala Thr Ser Gln
        2755            2760                2765

His Ser Pro Gly Ile Asp Lys Glu Asn Val Glu Leu Ser Pro Thr Thr
    2770            2775                2780

Gly His Cys Asn Ser Gly Arg Thr Arg His Gly Ser Ala Ser Gln Val
2785            2790            2795                2800

Gln Lys Gln Arg Ser Ala Gly Ser Phe Lys Arg Asn Ser Ile Lys Lys
            2805            2810                2815

Ile Val

<210> SEQ ID NO 3
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 3
tcaccaaagc tcagagcacg a                                          21

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 4
gccttgttgc aggatttgag t                                          21

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 5
atgaccatcc gcccagcata c                                          21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 6
gagaacgcag gcgaccgttg g                                          21
```